(12) United States Patent
Haveri

(10) Patent No.: US 11,779,724 B2
(45) Date of Patent: Oct. 10, 2023

(54) RESPIRATION SENSOR ATTACHMENT DEVICE

(71) Applicant: SunMed Group Holdings, LLC, Grand Rapids, MI (US)

(72) Inventor: Heikki Haveri, Huhmari (FI)

(73) Assignee: SunMed Group Holdings, LLC, Grand Rapids, MI (US)

( * ) Notice: Subject to any disclaimer, the term of this patent is extended or adjusted under 35 U.S.C. 154(b) by 638 days.

(21) Appl. No.: 16/898,228

(22) Filed: Jun. 10, 2020

(65) Prior Publication Data

US 2020/0390993 A1 Dec. 17, 2020

Related U.S. Application Data

(60) Provisional application No. 62/860,171, filed on Jun. 11, 2019.

(51) Int. Cl.
*A61M 16/06* (2006.01)
*A61M 16/00* (2006.01)

(52) U.S. Cl.
CPC .... *A61M 16/0672* (2014.02); *A61M 16/0003* (2014.02); *A61M 16/0616* (2014.02); *A61M 2016/0021* (2013.01)

(58) Field of Classification Search
CPC ..... A61B 5/6819; A61B 5/6803; A61B 5/087; A61B 5/097; A61B 5/0816; A61B 5/0878; A61M 16/0672; A61M 16/0003; A61M 16/0616; A61M 16/085; A61M 16/06; A61M 16/0683; A61M 16/0605; A61M 16/0666; A61M 16/0866; A61M 2016/0021; A61M 2016/0661
See application file for complete search history.

(56) References Cited

U.S. PATENT DOCUMENTS 4,201,205 A 5/1980 Bartholomew
4,263,908 A 4/1981 Mizerak
(Continued)

FOREIGN PATENT DOCUMENTS

CA 3064505 A1 11/2018
CN 203235110 U 10/2013
(Continued)

OTHER PUBLICATIONS

Canadian Office Action for Application No. 3141875, dated Oct. 4, 2022, 6 pages.
(Continued)

*Primary Examiner* — Samchuan C Yao
*Assistant Examiner* — Savannah L Gabriel
(74) *Attorney, Agent, or Firm* — Sheridan Ross P.C.

(57) ABSTRACT

A respiration sensor fluid delivery device is provided. The device includes first and second nasal exhalation flow passages that extend through the device, wherein the first and second nasal exhalation flow passages can be aligned in parallel to one another with respect to a nasal respiratory flow direction. A housing of the respiration sensor fluid delivery device fluidly couples with one of a nasal cannula assembly and a respiratory mask assembly. The device provides for respiration monitoring of a subject via a sensor and fluid delivery, such as oxygen, to the subject. Methods of using a respiration sensor fluid delivery device and fluid delivery devices are also provided.

20 Claims, 25 Drawing Sheets

(56) References Cited

U.S. PATENT DOCUMENTS

| | | | |
|---|---|---|---|
| 4,777,963 A | 10/1988 | McKenna | |
| 4,777,963 A | 10/1988 | McKenna | |
| 5,005,571 A | 4/1991 | Dietz | |
| 5,005,571 A | 4/1991 | Dietz | |
| 5,069,222 A | 12/1991 | McDonald, Jr. | |
| 5,069,222 A | 12/1991 | McDonald, Jr. | |
| 5,190,048 A | 3/1993 | Wilkinson | |
| 5,195,529 A | 3/1993 | Malkamaki | |
| 5,195,529 A | 3/1993 | Malkamaki | |
| 5,400,781 A | 3/1995 | Davenport | |
| 5,413,111 A | 5/1995 | Wilkinson | |
| 5,474,060 A | 12/1995 | Evans | |
| 5,485,850 A | 1/1996 | Dietz | |
| 5,485,850 A | 1/1996 | Dietz | |
| 5,671,733 A | 9/1997 | Raviv et al. | |
| 5,857,460 A | 1/1999 | Popitz | |
| 6,342,040 B1 | 1/2002 | Starr et al. | |
| 6,357,437 B1 | 3/2002 | Jacques | |
| 6,368,287 B1 | 4/2002 | Hadas | |
| 6,368,287 B1 | 4/2002 | Hadas | |
| 6,418,928 B1 | 7/2002 | Bordewick et al. | |
| 6,450,166 B1 | 9/2002 | McDonald et al. | |
| 6,491,034 B1 | 12/2002 | Gunaratnam et al. | |
| 6,595,207 B1 | 7/2003 | McDonald et al. | |
| 6,631,719 B2 | 10/2003 | McDonald et al. | |
| 6,811,538 B2 | 11/2004 | Westbrook et al. | |
| 6,837,238 B2 | 1/2005 | McDonald | |
| 7,024,235 B2 | 4/2006 | Melker et al. | |
| 7,024,235 B2 | 4/2006 | Melker et al. | |
| 7,063,084 B2 | 6/2006 | McDonald | |
| 7,087,027 B2 | 8/2006 | Page | |
| 7,087,027 B2 | 8/2006 | Page | |
| 7,114,498 B1 | 10/2006 | Nashed | |
| 7,533,670 B1 | 5/2009 | Freitag et al. | |
| 7,533,670 B1 | 5/2009 | Freitag et al. | |
| 7,806,120 B2 | 10/2010 | Loomas et al. | |
| 7,806,120 B2 | 10/2010 | Loomas et al. | |
| 7,856,979 B2 | 12/2010 | Doshi et al. | |
| 7,856,979 B2 | 12/2010 | Doshi et al. | |
| 7,909,035 B2 | 3/2011 | Thornton | |
| 8,020,558 B2 | 9/2011 | Christopher et al. | |
| 8,020,558 B2 | 9/2011 | Christopher et al. | |
| 8,042,540 B2 | 10/2011 | McDonald et al. | |
| 8,336,549 B2 | 12/2012 | Nashed | |
| 8,365,734 B1 | 2/2013 | Lehman | |
| 8,439,032 B2 | 5/2013 | Andrieux et al. | |
| 8,515,547 B2 | 8/2013 | Mass et al. | |
| 8,579,829 B2 | 11/2013 | Feldman et al. | |
| 8,591,430 B2 | 11/2013 | Amurthur et al. | |
| 8,616,203 B2 * | 12/2013 | Jaffe | A61M 16/0683 128/207.14 |
| 8,826,909 B2 | 9/2014 | Nashed | |
| 8,960,195 B2 | 2/2015 | Lehman | |
| 9,010,330 B2 | 4/2015 | Barlow et al. | |
| 9,022,029 B2 | 5/2015 | Varga et al. | |
| 9,044,565 B2 | 6/2015 | Colman et al. | |
| 9,138,169 B2 | 9/2015 | Beard | |
| 9,192,351 B1 | 11/2015 | Telfort et al. | |
| 9,250,104 B2 | 2/2016 | Greiner et al. | |
| 9,272,108 B2 | 3/2016 | Hu | |
| 9,339,621 B2 | 5/2016 | McAuley et al. | |
| 9,399,106 B2 | 7/2016 | Borody | |
| 9,486,598 B2 | 11/2016 | Takatori et al. | |
| 9,492,106 B2 | 11/2016 | Haveri | |
| 9,492,106 B2 | 11/2016 | Haveri | |
| 9,775,541 B2 | 10/2017 | Inoue | |
| 9,884,160 B2 | 2/2018 | McAuley et al. | |
| 10,004,865 B2 | 6/2018 | McAuley et al. | |
| 10,058,672 B2 | 8/2018 | Matsubara et al. | |
| 10,065,011 B2 | 9/2018 | Matsubara et al. | |
| 10,188,818 B2 | 1/2019 | Bowsher | |
| 10,265,487 B2 | 4/2019 | Booth Wise et al. | |
| 11,253,666 B2 * | 2/2022 | Beuchat | A61M 16/06 |
| 2003/0199945 A1 | 10/2003 | Ciulla | |
| 2007/0093724 A1 | 4/2007 | Nakano | |
| 2007/0093724 A1 | 4/2007 | Nakano | |
| 2007/0125380 A1 | 6/2007 | Acker et al. | |
| 2007/0125380 A1 | 7/2007 | Acker et al. | |
| 2007/0175473 A1 | 8/2007 | Lewis et al. | |
| 2007/0175473 A1 | 8/2007 | Lewis et al. | |
| 2007/0206907 A1 * | 9/2007 | Mizoguchi | H04B 10/2581 385/89 |
| 2007/0208269 A1 | 9/2007 | Mumford et al. | |
| 2008/0039739 A1 | 2/2008 | Buja | |
| 2000/8232604 | 9/2008 | Dufresne et al. | |
| 2008/0221470 A1 | 9/2008 | Sather et al. | |
| 2008/0221470 A1 | 9/2008 | Sather et al. | |
| 2008/0232604 A1 | 9/2008 | Dufresne et al. | |
| 2008/0232604 A1 * | 9/2008 | Dufresne | A61B 5/6843 381/67 |
| 2008/0243020 A1 | 10/2008 | Chou | |
| 2009/0069646 A1 | 3/2009 | Yamamori et al. | |
| 2009/0069646 A1 | 3/2009 | Yamamori et al. | |
| 2009/0099471 A1 | 4/2009 | Broadley et al. | |
| 2009/0133699 A1 | 5/2009 | Nalagatla et al. | |
| 2009/0133699 A1 | 5/2009 | Nalagatla et al. | |
| 2009/0203970 A1 | 8/2009 | Fukushima et al. | |
| 2009/0221888 A1 | 9/2009 | Wijesiriwardana | |
| 2009/0250061 A1 | 10/2009 | Marasigan | |
| 2009/0306528 A1 | 12/2009 | Curti et al. | |
| 2009/0306528 A1 | 12/2009 | Curti et al. | |
| 2009/0306529 A1 * | 12/2009 | Curti | A61B 5/4818 128/204.23 |
| 2009/0318781 A1 | 12/2009 | Henke et al. | |
| 2010/0113956 A1 | 5/2010 | Curti et al. | |
| 2010/0113956 A1 | 5/2010 | Curti et al. | |
| 2010/0163043 A1 | 7/2010 | Hart et al. | |
| 2010/0252037 A1 | 10/2010 | Wondka et al. | |
| 2010/0252042 A1 | 10/2010 | Kapust et al. | |
| 2010/0252042 A1 | 10/2010 | Kapust et al. | |
| 2011/0066061 A1 | 3/2011 | Colman et al. | |
| 2011/0094513 A1 * | 4/2011 | Takatori | A61M 16/0875 128/202.16 |
| 2011/0108041 A1 | 5/2011 | Sather et al. | |
| 2011/0108041 A1 | 5/2011 | Sather et al. | |
| 2011/0125052 A1 | 5/2011 | Davenport et al. | |
| 2011/0125052 A1 | 5/2011 | Davenport et al. | |
| 2011/0197689 A1 | 8/2011 | Haveri et al. | |
| 2011/0218451 A1 | 9/2011 | Lai et al. | |
| 2011/0218451 A1 | 9/2011 | Lai et al. | |
| 2011/0290256 A1 | 12/2011 | Sather et al. | |
| 2011/0290256 A1 | 12/2011 | Sather et al. | |
| 2011/0301484 A1 | 12/2011 | Curti et al. | |
| 2012/0052469 A1 | 3/2012 | Sobel et al. | |
| 2012/0132208 A1 | 5/2012 | Judson et al. | |
| 2012/0203128 A1 | 8/2012 | Levison et al. | |
| 2012/0257561 A1 | 10/2012 | Redding | |
| 2012/0289851 A1 | 11/2012 | Varga et al. | |
| 2013/0032148 A1 | 2/2013 | Neely | |
| 2014/0238400 A1 | 8/2014 | Miller | |
| 2014/0275857 A1 | 9/2014 | Schwartz | |
| 2014/0366890 A1 | 12/2014 | Tao et al. | |
| 2015/0099986 A1 * | 4/2015 | Inoue | A62B 9/006 600/479 |
| 2015/0202473 A1 | 7/2015 | Curran et al. | |
| 2015/0209533 A1 | 7/2015 | Boussignac | |
| 2015/0217075 A1 | 8/2015 | Nair | |
| 2015/0313535 A1 | 11/2015 | Alshaer et al. | |
| 2016/0029148 A1 | 1/2016 | Jackson et al. | |
| 2016/0030695 A1 | 2/2016 | Chang | |
| 2016/0045161 A1 | 2/2016 | Alshaer et al. | |
| 2016/0150981 A1 | 6/2016 | Baker et al. | |
| 2016/0210099 A1 | 7/2016 | Hampapuran et al. | |
| 2016/0271351 A1 | 9/2016 | Frater et al. | |
| 2016/0345893 A1 | 12/2016 | Von Janecek et al. | |
| 2017/0007795 A1 | 1/2017 | Pedro et al. | |
| 2017/0007795 A1 | 1/2017 | Pedro et al. | |
| 2017/0020444 A1 | 1/2017 | Lurie | |
| 2017/0028154 A1 | 2/2017 | Takatori et al. | |
| 2017/0028231 A1 | 2/2017 | Zhao et al. | |
| 2017/0079580 A1 | 3/2017 | Moore et al. | |
| 2017/0147772 A1 | 5/2017 | Meehan et al. | |
| 2017/0151406 A1 | 6/2017 | Booth Wise et al. | |
| 2017/0151409 A1 | 6/2017 | Peacock et al. | |

(56) References Cited

U.S. PATENT DOCUMENTS

| | | |
|---|---|---|
| 2017/0173262 A1 | 6/2017 | Veltz |
| 2017/0189635 A1 | 7/2017 | Beard |
| 2017/0196512 A1 | 7/2017 | Inoue |
| 2018/0008849 A1 | 1/2018 | Baker |
| 2018/0043121 A1 | 2/2018 | Goulitski et al. |
| 2018/0146887 A1 | 5/2018 | Cheng |
| 2018/0172664 A1 | 6/2018 | Love et al. |
| 2018/0279881 A1 | 10/2018 | McCalmont et al. |
| 2019/0116088 A1 | 4/2019 | Mueglitz et al. |
| 2019/0174574 A1 | 6/2019 | Filgueiras et al. |
| 2020/0305760 A1 | 10/2020 | Naser |
| 2021/0268224 A1* | 9/2021 | White ............... A61M 16/0816 |

FOREIGN PATENT DOCUMENTS

| | | |
|---|---|---|
| CN | 203591509 U | 5/2014 |
| CN | 104523276 A | 4/2015 |
| CN | 106039517 A | 10/2016 |
| EP | 0604564 B1 | 7/1994 |
| EP | 0604564 B1 | 7/1994 |
| EP | 1044037 B1 | 10/2000 |
| EP | 1044037 B1 | 10/2000 |
| EP | 1095269 B1 | 5/2001 |
| EP | 1804875 B1 | 7/2007 |
| EP | 2015815 A4 | 1/2009 |
| EP | 2186539 B1 | 5/2010 |
| EP | 2236080 A1 | 10/2010 |
| EP | 2236080 A1 | 10/2010 |
| EP | 2319569 B1 | 5/2011 |
| EP | 2753392 B1 | 7/2014 |
| EP | 2859845 | 4/2015 |
| EP | 2890438 B1 | 7/2015 |
| EP | 2890463 B1 | 7/2015 |
| EP | 2903515 A1 | 8/2015 |
| EP | 2913003 A1 | 9/2015 |
| EP | 3166675 | 5/2017 |
| GB | 2506621 | 4/2014 |
| JP | 2006320731 A | 11/2006 |
| JP | 2006320732 A | 11/2006 |
| JP | 4607799 | 1/2011 |
| JP | 6293760 B2 | 10/2015 |
| JP | 2016000157 A | 1/2016 |
| JP | 2018509947 A | 4/2018 |
| JP | 6329975 | 5/2018 |
| JP | 2019513061 A | 5/2019 |
| WO | WO-9934864 A1 | 7/1999 |
| WO | WO-9934864 A1 | 7/1999 |
| WO | WO-2006026387 A2 | 3/2006 |
| WO | WO-2006026387 A2 | 3/2006 |
| WO | WO-2007128100 A1 | 11/2007 |
| WO | WO-2012094730 | 7/2012 |
| WO | WO-2013043847 A1 | 3/2013 |
| WO | WO-2016185470 A1 | 11/2016 |
| WO | WO-2016185470 A1 | 11/2016 |
| WO | WO-2017131607 | 8/2017 |
| WO | WO-2017199089 A2 | 11/2017 |
| WO | WO-2017199089 A2 | 11/2017 |
| WO | WO-2018017565 | 1/2018 |
| WO | WO-2018029689 | 2/2018 |
| WO | WO-2018071699 A1 | 4/2018 |

OTHER PUBLICATIONS

Australian Office Action for Application No. 2020290445, dated Sep. 9, 2022, 2 pages.
Extended European Search Report for Application No. 22168445.9, dated Aug. 3, 2022, 10 pages.
Japanese Office Action for Application No. 2021-570381, dated Oct. 6, 2022, 6 pages including translation.
International Preliminary Report on Patentability for Application No. PCT/US2020/037060, dated Jul. 19, 2021, 18 pages.
Invitation to Pay Additional Fees for Application No. PCT/US2018/065247, dated Mar. 14, 2019, 15 pages.
Avalur, Divya S., "Human Breath Detection using a Microphone", Master's thesis, University of Groningen, Faculty of Mathematics and Natural Sciences, Aug. 30, 2013, 67 pages.
Binu, E. et al., Real Time Monitoring of Respiratory Parameters Using a Wireless Portable System, International Journal of Engineering Development and Research, 2014, vol. 3, Issue 1, ISSN: 23-21-9939, pp. 283-287.
International Search Report and Written Opinion for Application No. PCT/US2018/065247, dated Jun. 5, 2019, 23 pages.
International Search Report and Written Opinion for Application No. PCT/US2019/044213, dated Nov. 7, 2019, 20 pages.
Jinesh, Matthew, et al. "A miniature optical breathing sensor", Biomed Opt Express. Dec. 1, 2012; 3(12): 3325-3331. Published online Nov. 26, 2012. doi: 10.1364/BOE.3.003325.
Invitation to Pay Additional Fees for Application No. PCT/US2018/065247, dated Mar. 14, 2019, 15 pages.

\* cited by examiner

RESPIRATION SENSOR ATTACHMENT DEVICE

CROSS-REFERENCE TO RELATED APPLICATIONS

This application claims the benefit of U.S. Provisional Application No. 62/860,171, filed on Jun. 11, 2019, the disclosure of which is hereby incorporated by reference in its entirety for all purposes.

BACKGROUND

The present disclosure relates generally to medical sensor attachment devices. More particularly, the present disclosure relates to devices for attaching respiration sensors to nasal cannulas and respiration masks.

The respiration of a person receiving fluid delivery (e.g., oxygen) via a nasal cannula or a respiration mask may be monitored for various reasons. For example, knowledge about a patient's respiration may assist a caregiver in assessing the patient's stability during surgery and recovery thereafter. Knowledge about a person's respiration can also assist with therapy related to sleeping.

Typical approaches to respiration sensors involve cumbersome devices that can obstruct a patient's respiratory passages and/or obstruct delivery of therapeutic gas to the patient via the cannula or mask. In many applications, the patient is unconscious or semi-conscious and there is a challenge to fix a cannula/mask in combination with a respiration sensor in place for an extended period of time. Accordingly, in many of the existing systems a nurse is required to choose between using a sensor device or a cannula/mask at any given time, or to manually place and adjust the positioning of separate sensor and fluid delivery devices. Moreover, the nurse must frequently check the patient for sensor placement or movement relative to the cannula/mask in order to ensure the sensor device is not blocking or hindering delivery of a therapeutic gas to the patient.

SUMMARY

In the field of medical care for patients with respiratory dysfunction, it is highly desirable to provide continuous, real-time measurement of the patient's respiratory cycles in combination with delivery of a therapeutic fluid to the patient. In the measurement of respiratory cycles from patients combined with fluid delivery, one of the challenges is to position both the sensor device and the fluid delivery device (e.g., cannula/mask) such that neither device interferes with the operation of the other device. The complication is compounded by the human physiognomy and patient movement, which makes it difficult to keep both a sensor device and a fluid delivery device properly positioned on the patient's face and in relation to each other.

An aspect of the present disclosure provides, but is not limited to, a connection assembly for combining a fluid delivery device and a respiration sensor for monitoring of a patient's respiratory condition and cycle.

In some embodiments, the present disclosure provides a respiration sensor cannula device including a base and a housing comprising first and second nasal exhalation flow passages, the first and second nasal exhalation flow passages are aligned in parallel to one another with respect to a nasal respiratory flow direction. The housing includes first and second openings in an outer surface of the housing, and first and second nasal inhalation flow passages extending from the first and second openings, respectively. The first and second openings are configured to receive a gas from a fluid delivery tube.

In some embodiments, the present disclosure provides a respiration sensor mask device including a base and a housing comprising first and second nasal exhalation flow passages, the first and second nasal exhalation flow passages are aligned in parallel to one another with respect to a nasal respiratory flow direction. The respiration sensor cannula device includes first and second openings in an outer surface of the housing, and the respiration sensor cannula device includes first and second nasal inhalation flow passages. The housing is configured to fluidly couple with a nasal cannula assembly, and the first and second openings are configured to receive the first and second nasal inhalation flow passages therethrough, respectively.

In some embodiments, the present disclosure provides a respiration sensor mask device including a base and a housing comprising first and second nasal exhalation flow passages, the housing comprising a connection recess, wherein the first and second nasal exhalation flow passages are aligned in parallel to one another with respect to a nasal respiratory flow direction. The respiration sensor cannula device includes a connection band comprising a connection member extending from the connection band, wherein the connection member is configured to couple with the connection recess. The respiration sensor cannula device includes a respiration mask coupled between the connection band and the housing.

In some embodiments, the present disclosure provides a method of using a respiration sensor device with a fluid delivery device. The method includes placing the respiration sensor device on a subject, the respiration sensor device having a base and a housing comprising first and second nasal exhalation flow passages that are disposed in parallel to one another with respect to a nasal respiratory flow direction; positioning the respiration sensor device so that first and second nasal thermistors in the respective first and second nasal exhalation flow passages receive exhalations from the subject's nares. The method also includes connecting the fluid delivery device to the respiration sensor device, wherein the respiration sensor device and the fluid delivery device are disposed as a unit on the subject's face, and wherein the fluid delivery device comprises any of a cannula or a respiration mask; replacing the fluid delivery device with the other of the cannula or the respiration mask without removing the respiration sensor device from the subject.

In some embodiments, the present disclosure provides a method of using a respiration sensor device with a fluid delivery device. The method includes providing a respiration sensor device comprising first and second nasal exhalation flow passages, the first and second nasal exhalation flow passages are aligned in parallel to one another with respect to a nasal respiratory flow direction. The method also includes coupling a fluid delivery device comprising a respiration mask to the respiration sensor device such that the respiration sensor device is positioned within an interior volume of the respiration mask, the respiration mask configured to provide an area of higher gas concentration in a first portion of the interior volume of the respiration mask, relative to a second portion of the interior volume of the respiration mask, wherein at least a portion of the respiration sensor device is positioned in the first portion of the interior volume of the respiration mask.

In some embodiments, the present disclosure provides a method of using a respiration sensor device with a fluid delivery device. The method includes providing a nasal inhalation flow passage of a nasal cannula proximal to a septum of the subject's nares. The method also includes providing a sensor of a respiration sensor device laterally outward relative to the nasal inhalation flow passage. A fluid flow path from the nasal inhalation flow passage toward a subject's nare does intersect the sensor.

In some embodiments, the present disclosure provides a respiration sensor system. The system includes a respiration sensor device comprising an attachment mechanism configured to couple with any of a nasal cannula assembly and a respiration mask. The respiration sensor device can comprise first and second nasal exhalation flow passages. The respiration sensor device is configured to remain worn by a patient during interchange of the nasal cannula assembly and the respiration mask.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures.

In the figures, elements having the same or similar reference numeral have the same or similar functionality or configuration, unless expressly stated otherwise.

DETAILED DESCRIPTION

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings, and detailed description are to be regarded as illustrative in nature and not as restrictive.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. It will be apparent, however, to one ordinarily skilled in the art that the embodiments of the present disclosure may be practiced without some of these specific details. In other instances, well-known structures and components are shown in block diagram form in order to avoid obscuring the concepts of the subject technology, or have not been shown in detail so as not to obscure the disclosure. Like components are labeled with similar element numbers for ease of understanding.

In accordance with at least some embodiments disclosed herein are connection assemblies for combining a respiration sensor device and a fluid delivery device (e.g., nasal cannula, respiration mask). In at least some embodiments disclosed herein, methods of connecting respiration sensor and fluid delivery devices are disclosed.

Figure 1:
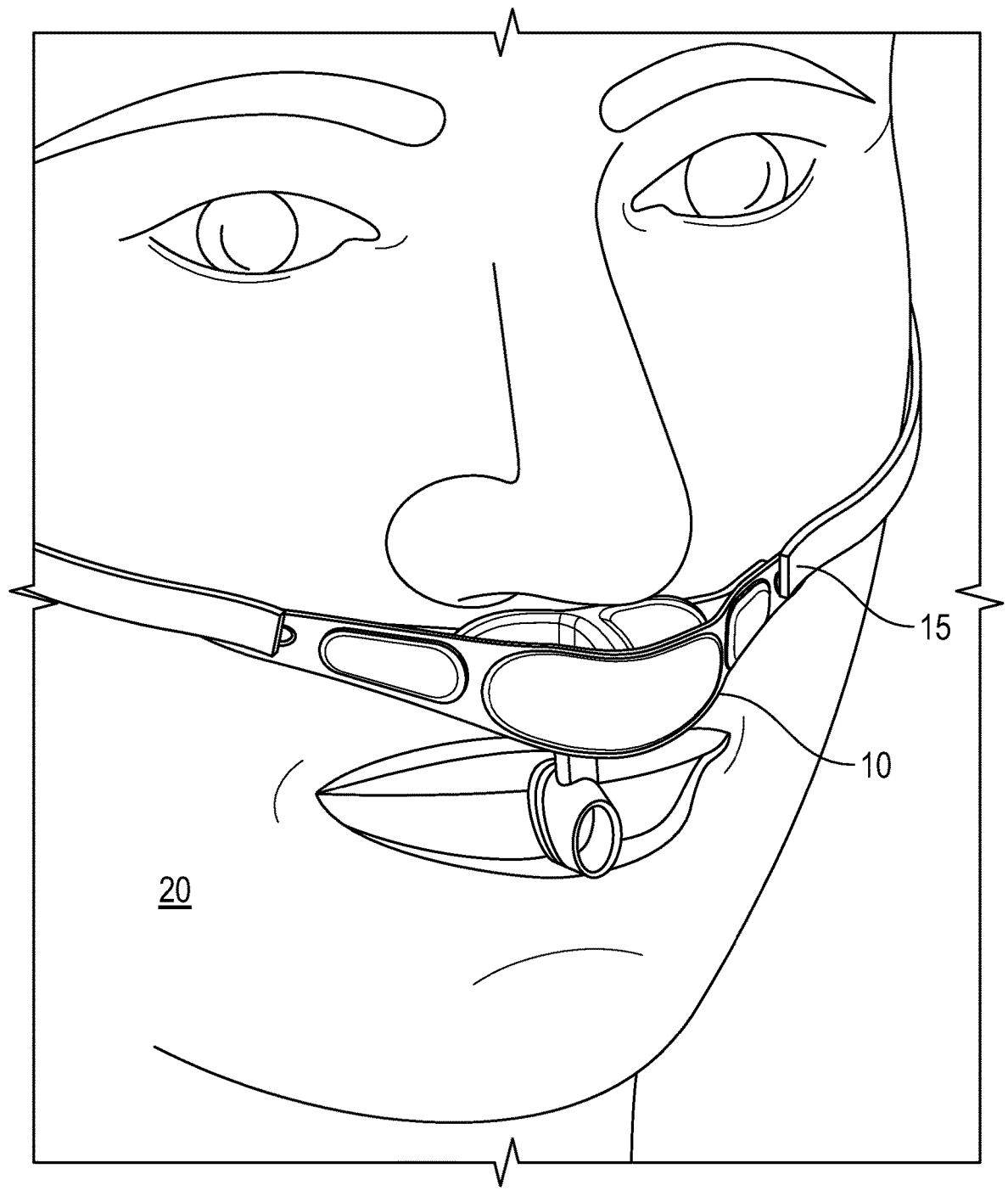
FIG. 1 illustrates a front perspective view of a respiration sensor device placed on a patient's head.

FIG. 1 illustrates a respiration sensor 10 placed on a patient's head 20, according to some embodiments. The respiration sensor 10 is positioned on patient's face between the mouth and nose to measure nasal and oral breathing gas flow. A securement string or strap 15 helps maintain the position of respiration sensor 10 relative to the patient's physiognomy.

Figure 2:
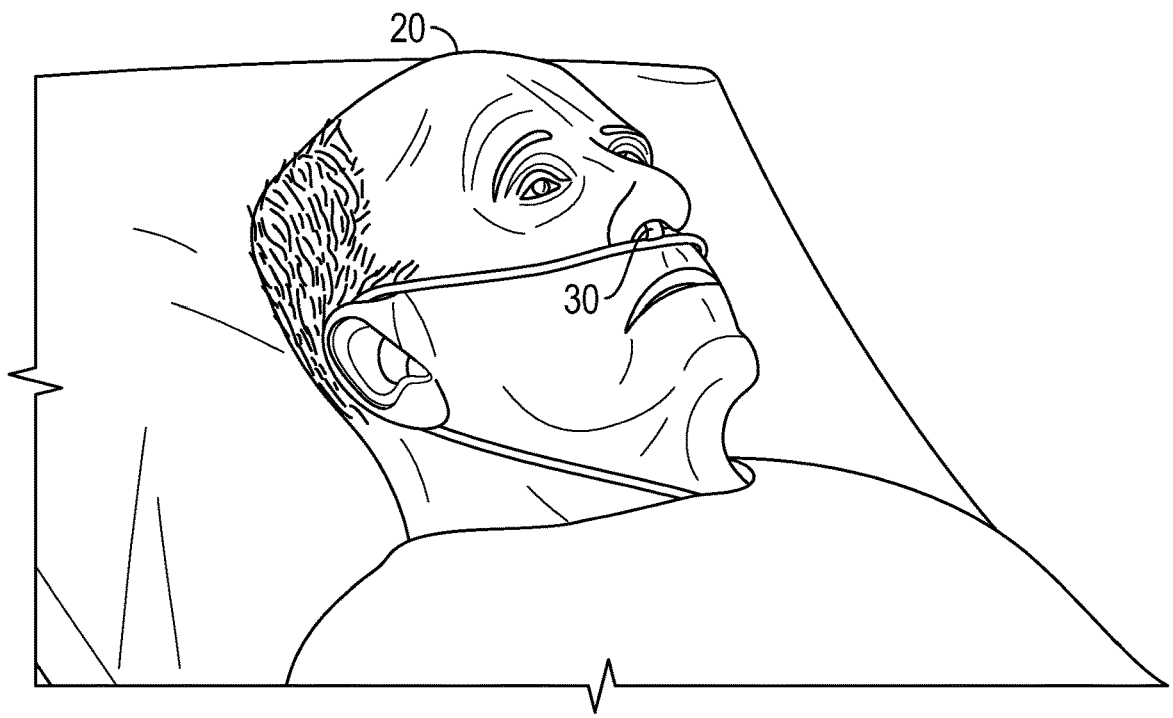
FIG. 2 illustrates a front perspective view of a nasal cannula placed on a patient's head.
Figure 3:
FIG. 3 illustrates a front perspective view of a respiration mask placed on a patient's head.

FIGS. 2 and 3 illustrate a typical nasal cannula 30 and a typical respiratory mask 40 placed on a patient's head 20, respectively. Here, the nasal cannula 30 and the respiratory mask 40 deliver a fluid, such as oxygen, to the patient. The fluid delivery may be for therapeutic purposes (e.g., deliver oxygen to assist in patient's respiratory function), for delivery of medication via inhalation, for respiratory testing and/or for any other respiratory functions.

Figure 4A:
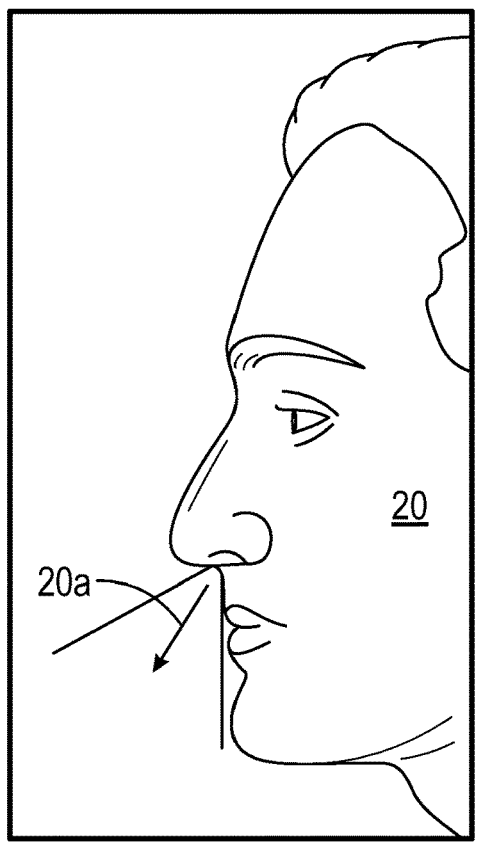
FIG. 4A illustrates a side plan view of a gas flow exiting from a patient's nasal cavity.
Figure 4B:
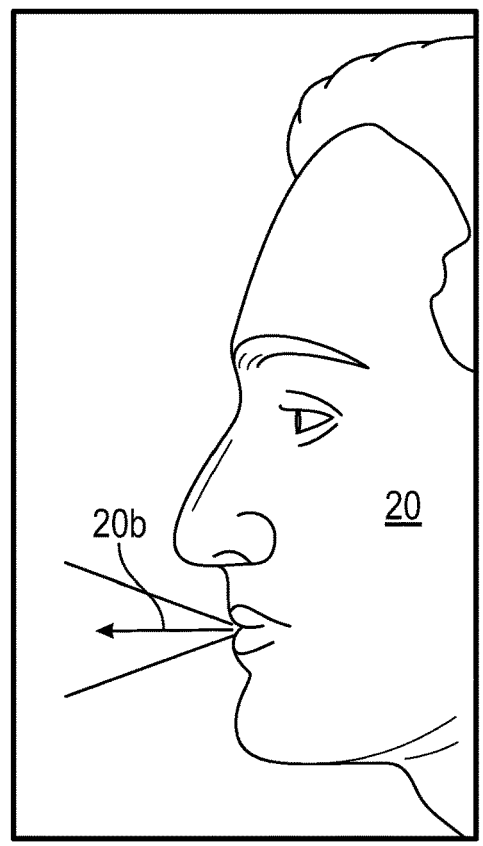
FIG. 4B illustrates a side plan view of a gas flow exiting from a patient's oral cavity.
Figure 5:
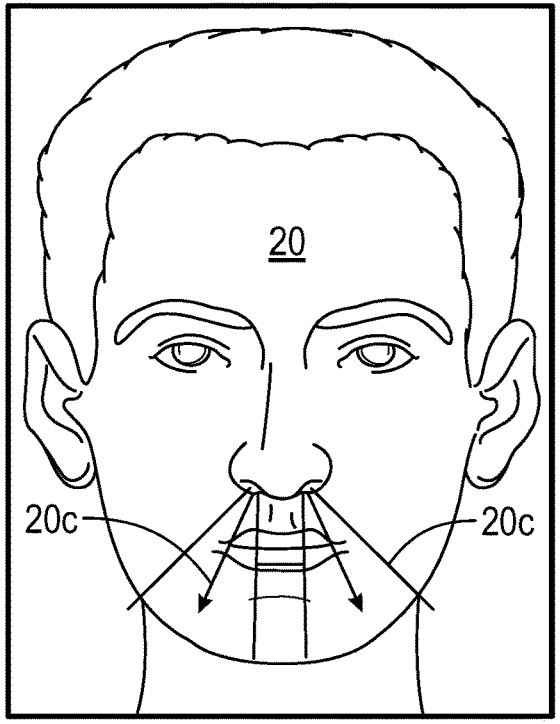
FIG. 5 illustrates a front plan view of a gas flow exiting from a patient's nasal cavity.

FIGS. 4A and 5 illustrate regions 20a, 20c for a gas flow exiting from a patient's nasal cavities, and FIG. 4B illustrates regions 20b for a gas flow exiting from a patient's oral cavity, according to some embodiments. Experiments show that breathing gas flow exits nasal and oral cavities in different regions between different subjects. Accordingly, a respiration sensor may include a geometry that separates each of the different flows through the regions 20a, 20b, 20c to provide an accurate measure of the respiratory cycles of a patient. Accordingly, proper positioning of the respiration sensor 10 relative to a nasal cannula 30 or a respiratory mask 40 and relative to the patient's face is highly desirable.

Figure 6:
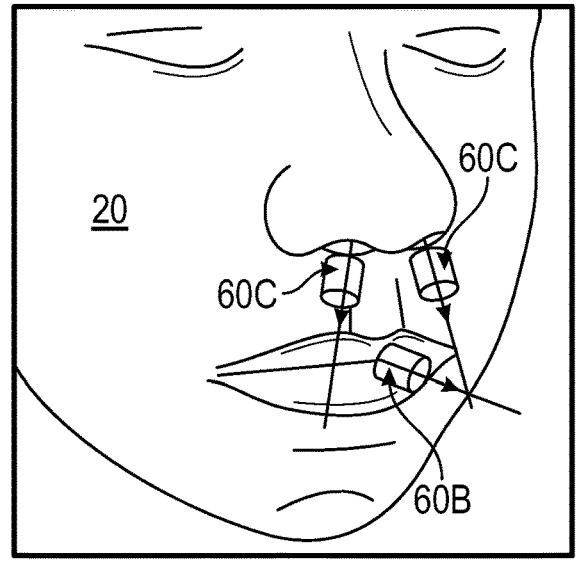
FIG. 6 illustrates a front perspective view of nasal respiration flows and oral respiration flows in a patient.
Figure 7A:
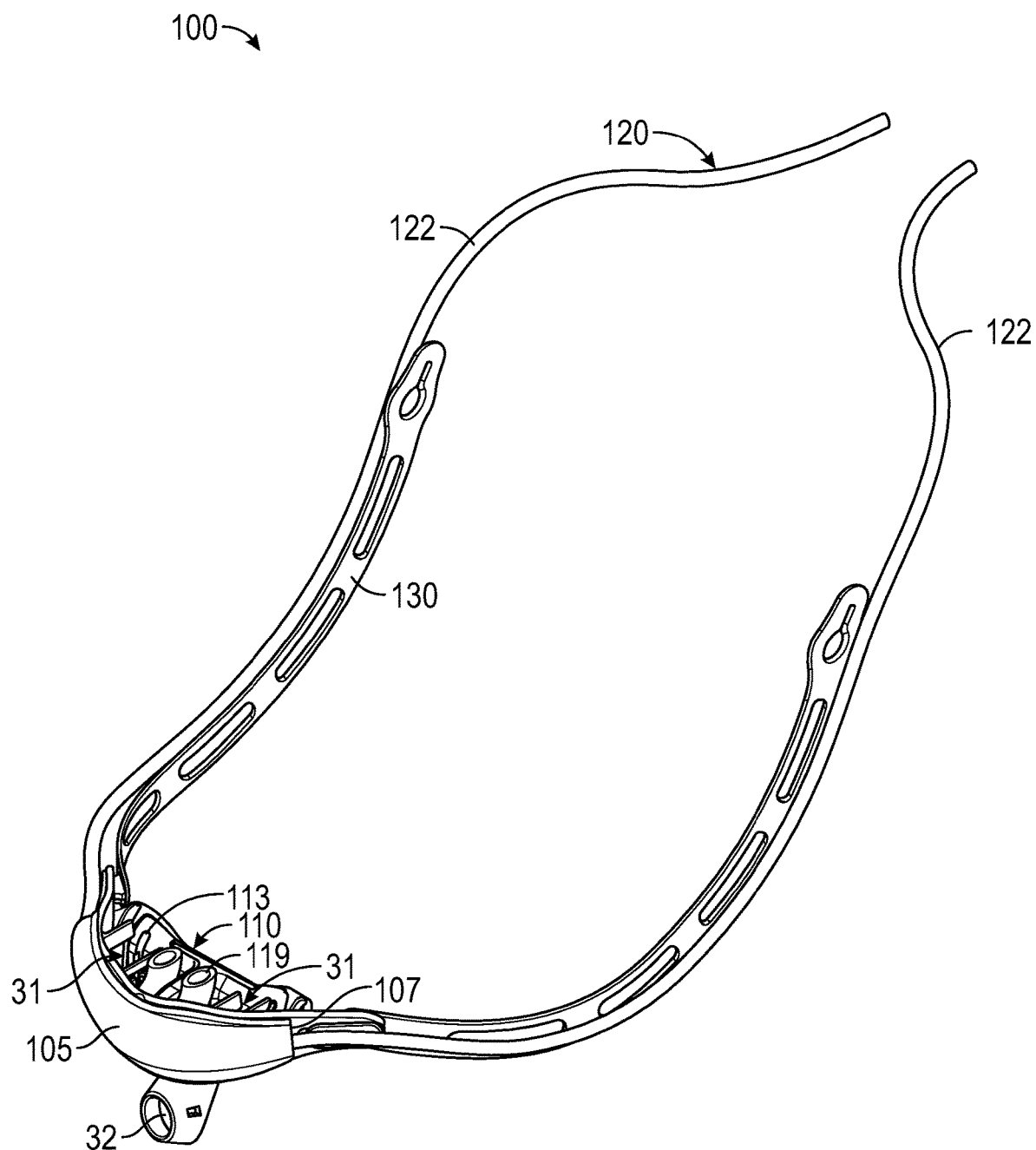
FIG. 7A illustrates a front perspective view of a respiration sensor cannula device, according to some embodiments.
Figure 7B:
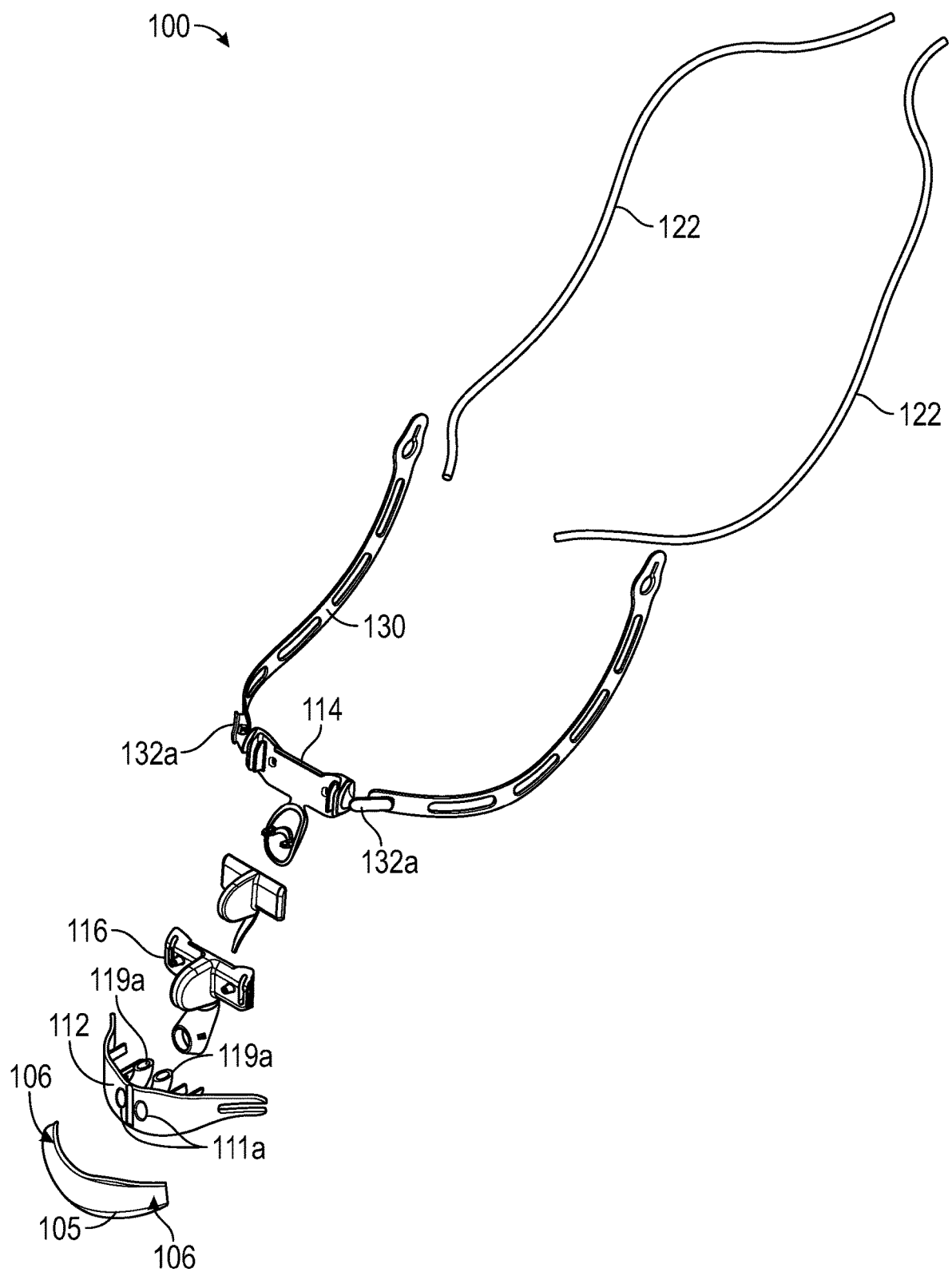
FIG. 7B is an exploded view of FIG. 7A.

FIG. 6 illustrates a portion of nasal respiration flow 60C and oral respiration flow 60B for a patient 20. Sensor cavities of the respiration sensor capture nasal and oral breathing gas flow from the patient. The sensor cavities are positioned parallel to the average direction of that specific flow to maintain flow as laminar as possible inside the cavity. Thus, nasal sensor cavities are positioned parallel to each other between the nose and mouth, but also parallel to upper lip. More advantageously, nasal sensor cavities slightly diverge past the middle part of the mouth and upper lip into the average direction of nasal breathing gas flows. An oral sensor cavity is positioned transverse to the nasal cavities, outwards from the mouth. In some embodiments, the oral sensor cavity and the nasal sensor cavities are positioned relative to each other so that a direction of oral respiration flow 60B through the oral cavity is transverse relative to a direction of nasal respiration flow 60C through any of the nasal sensor cavities. Sensor cavities are also smooth and straight, or more advantageously slightly tapered, to capture flow from a larger area, since any turn or sudden change in the cross-section of cavity along the flow path generate turbulences that mix inspiratory and expiratory air flow phases degrading the measurement speed, accuracy and response time.

FIGS. 7A-12 illustrate a respiration sensor cannula device 100 having a respiration sensor device 110 with nasal flow passages (e.g., exhalation flow passage) 31 and an oral flow passage (e.g., cavity) 32, and a nasal cannula assembly 120. The nasal cannula assembly 120 includes delivery tubes 122 for delivering a fluid (e.g., gas) from a fluid source (not shown) to the individual or patient wearing the respiration sensor cannula device 100. The nasal respiration flow exiting a patient's nasal cavity, e.g., gas flow regions 20a, 20c, can be captured and guided by a nasal flow passage 31 parallel to average direction of nasal respiration flow 60C. Similarly, the oral respiration flow exiting a patient's mouth, e.g., gas flow region 20b, can be captured and guided by the oral cavity 32 parallel to direction of the oral respiration flow 60B.

Figure 10:
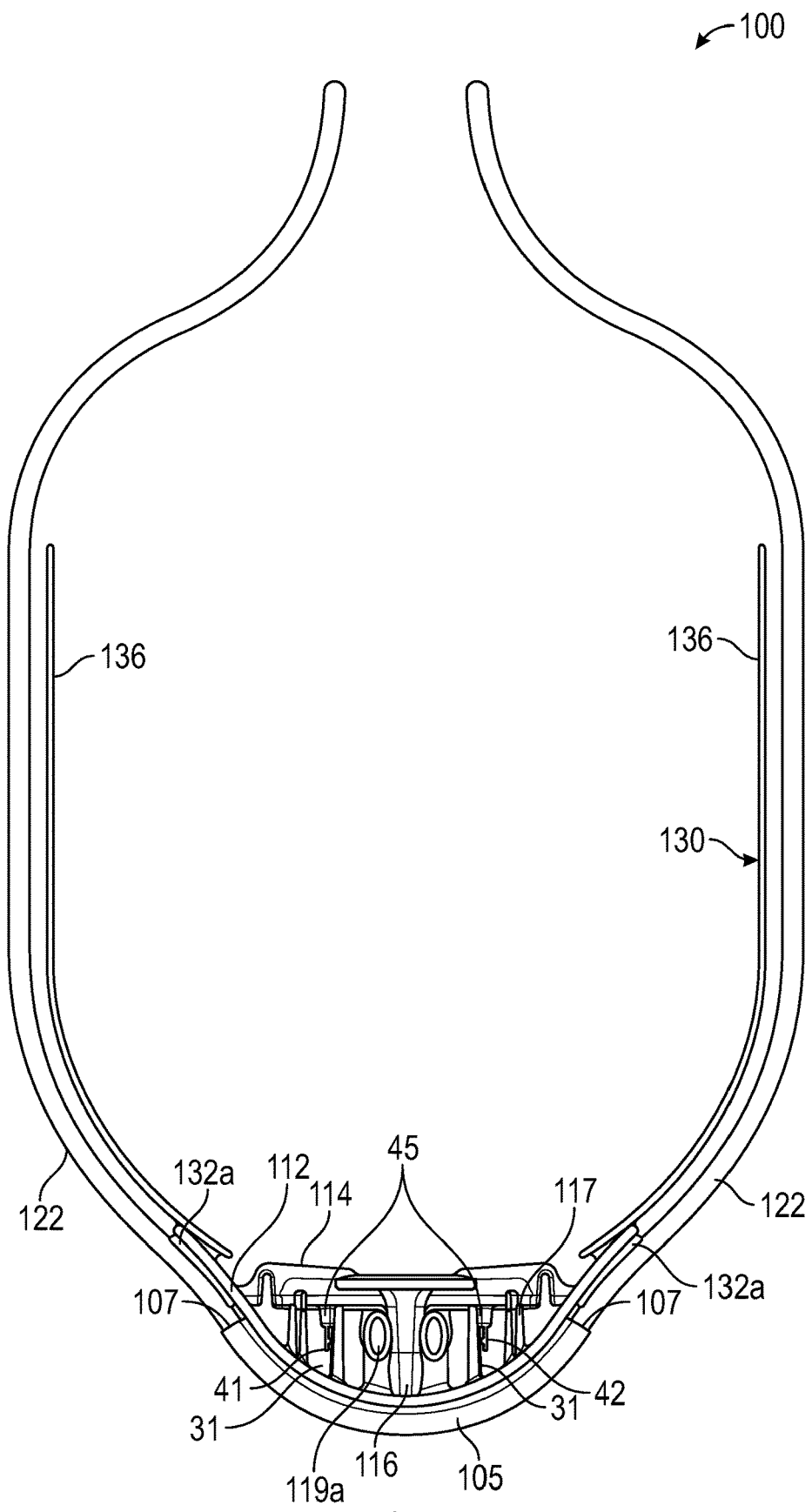
FIG. 10 illustrates a top view of the respiration sensor cannula device of FIG. 7.
Figure 12:
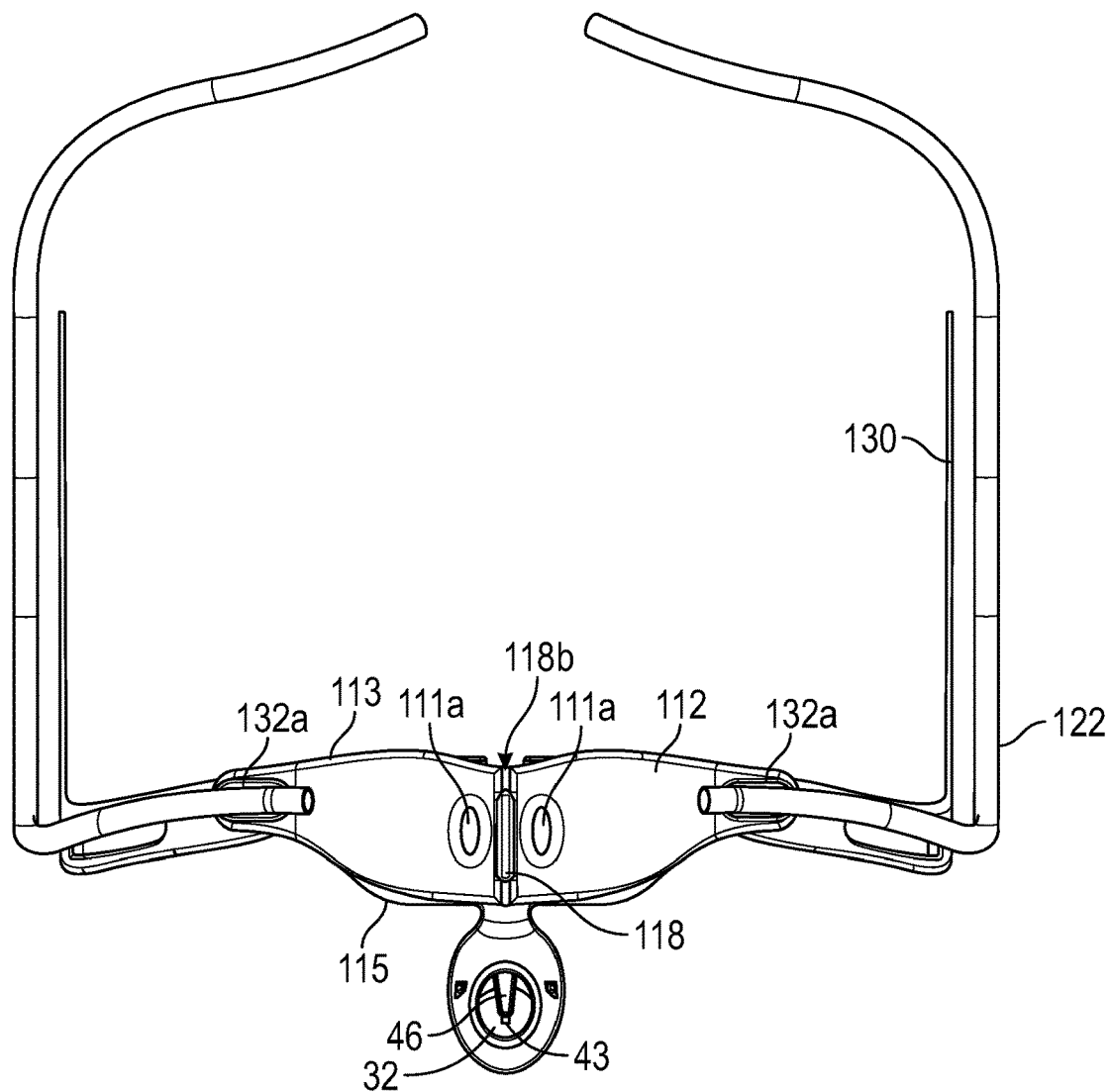
FIG. 12 illustrates a front plan view of the respiration sensor cannula device of FIG. 7A with the cover removed.
Figure 13:
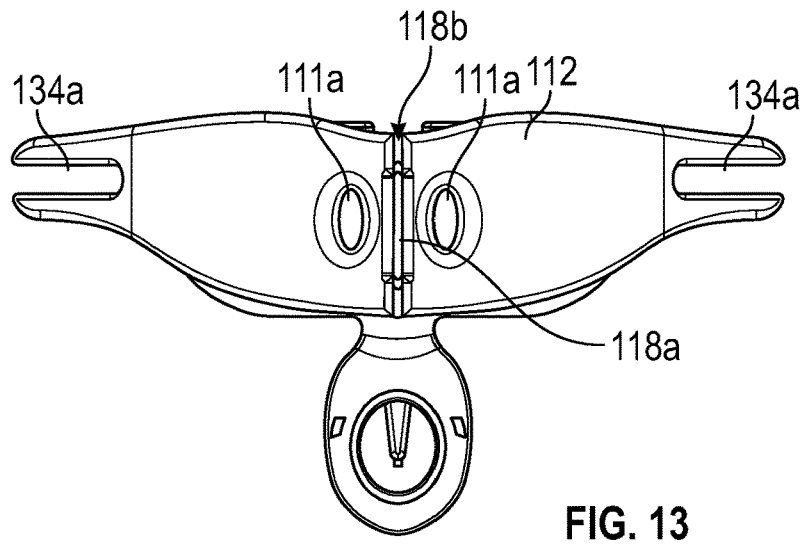
FIG. 13 illustrates a front plan view of a respiration sensor device, according to some embodiments.

By providing a sensor element (e.g., thermistors) inside of each of the different flow passages 31 and 32, the respiration sensor device 110 may accurately determine a respiration flow before the nasal flow and the oral flows are mixed together adjacent the patient's upper lip. For example, the respiration sensor device 110 includes thermistors 41, 42, 43 for sensing inhalation and exhalation flows (FIGS. 10, 12). A nasal respiratory flow of a patient can be captured by the nasal flow passages 31 and measured with a first and second nasal thermistors 41, 42 therein. An oral respiratory flow of the patient can be captured by the oral cavity 32 and measured with thermistor 43 therein. The resistance of each thermistor 41, 42, 43 changes proportionally to flowing gas heating or cooling down the thermistor 41, 42, 43 (e.g., during inspiration and expiration).

Moreover, the nasal flow passages 31 are separated from each other such that nasal thermistors 41 and 42 may separately identify and measure the respiration flow associated with each of the patient's nostrils. By separately identifying respiration flow associated with each of the patient's nostrils, potential respiratory conditions or patient's positions can be determined. For example, a blockage of a nasal passage or the respiration device can be identified and corrected.

In some embodiments, oral thermistor 43 is placed on a plane that is transverse or substantially perpendicular to nasal thermistors 41, 42. This geometry also enables an accurate and independent measurement between each of the thermistors 41, 42, 43, avoiding any mixing or turbulent area. The thermistors 41, 42, 43 can be located approximately in the middle of its corresponding flow passage 31, 32 to maximize accuracy and sensitivity to gas flows. To position the nasal thermistor 41, 42 in the middle of a corresponding flow passage 31, the nasal thermistor 41, 42 is coupled to a tip portion of a corresponding support structure 45. To position the oral thermistor 43 in the middle of a corresponding flow passage 32, the oral thermistor 43 is coupled to a tip portion of a corresponding support structure 46. The support structure 45 for the nasal thermistor 41, 42 can have a proximal portion coupled to an electronics board and a distal portion transverse to a plane defined by the top of the electronics board, wherein the distal portion of the support structure 45 extends into a nasal flow passage 31. In some embodiments, the respiration sensor device 110 has a structure and geometry that separates the nasal flow from each nostril separately, to provide a more accurate and detailed picture of the patient's respiratory condition. Similarly, the support structure 46 for the oral thermistor 43 can have a proximal portion coupled to the electronics board and a distal portion parallel to a plane defined by the top of the electronics board, wherein the distal portion of the support structure 46 extends into oral cavity 32.

Some embodiments may include additional sensors, such as capacitive detectors or sensors to detect whether the respiration sensor device 110 is making proper contact with the patient's physiognomy and accelerometers to detect movement and position of the respiration sensor device 110 to ensure, for example, that the respiration sensor device 110 has not fallen out of place, that the patient has not fallen down, or that the orientation of the patient's head is not obstructing the nasal and oral breathing gas flows (e.g., patient's face is downward towards pillow or bed).

The respiration sensor device 110 may include a housing 112, a base 114, and a shroud 116. The shroud 116 is positioned between the housing 112 and the base 114 to form at least a portion of a cavity. As shown in FIG. 8, the area between the shroud 116 and the housing 112 is divided into two distinct nasal flow passages 31, such that the nasal thermistor 41 is centrally disposed in one of the nasal flow passages 31 and the nasal thermistor 42 is centrally disposed in the other one of the nasal flow passages 31. The nasal flow passages 31 extend from a top portion to a bottom portion of the respiration sensor device 110. In use, a nasal respiration flow from a patient's nose can move between a nasal inlet 113 and a nasal outlet 115 of each of the nasal flow passages 31. The nasal inlet 113 of each of the nasal flow passages 31 is where the breathing gas flows into the respiration sensor device 110 during expiration. The nasal outlet 115 of each of the nasal flow passages 31 is where the ambient air flows into the respiration sensor device 110 during inspiration.

Figure 11:
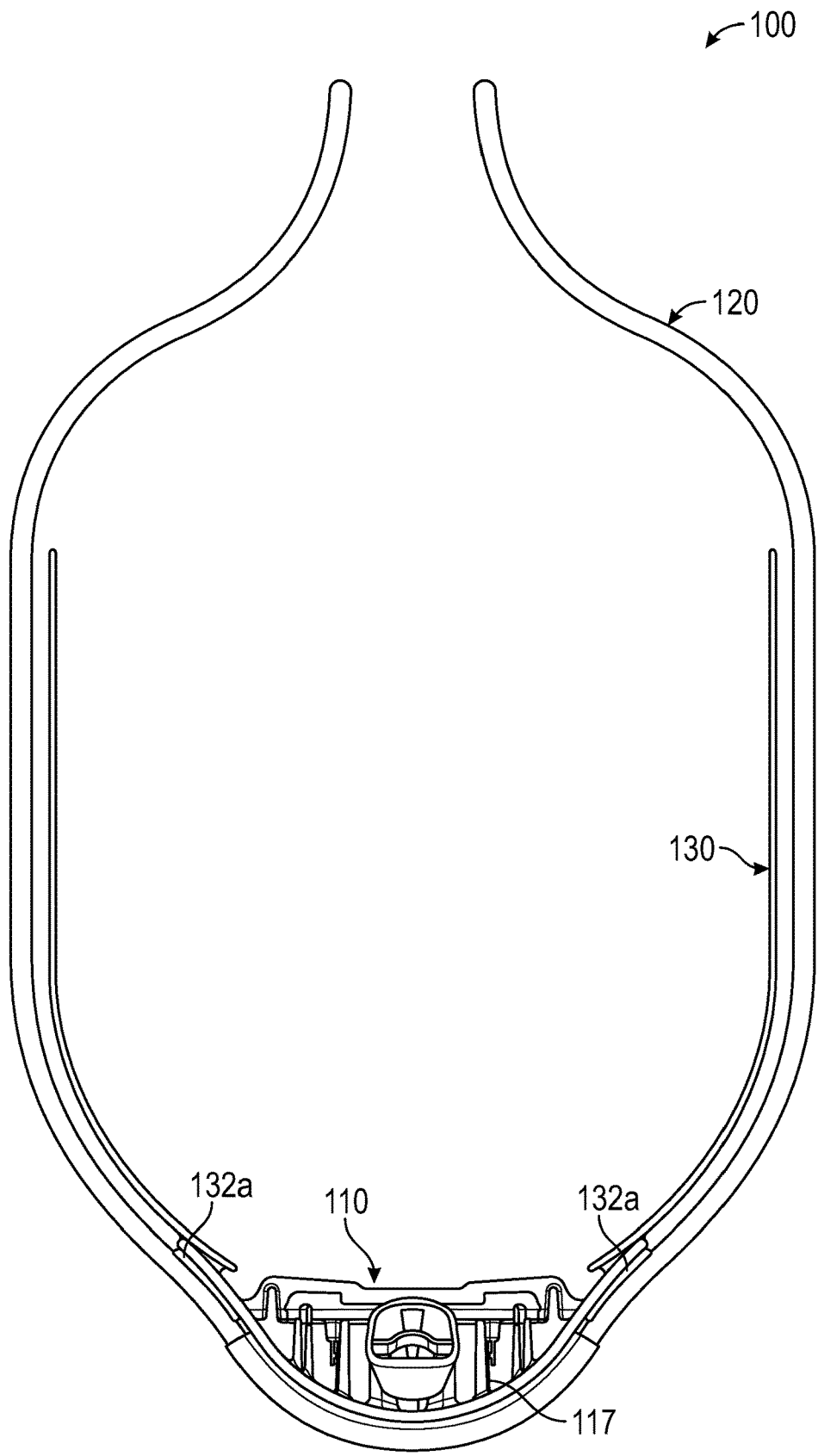
FIG. 11 illustrates a bottom view of the respiration sensor cannula device of FIG. 7A.

An outer surface of the housing 112 has openings 111a that provide an inlet path for the fluid delivered by the delivery tubes 122 (FIGS. 8, 10, 11). A cover 105 is coupled to the housing 112. The cover 105 has inlet ports (e.g., tube openings) 107 for receiving an end portion of the delivery tubes 122. For example, oxygen may flow through the delivery tubes 122 into an inner cavity defined by the cover 105 and the housing 112, and then into the openings 111a. Here, the cover 105 is shaped such that the fluid flow is guided from the end of the delivery tube 122 and along the inner cavity into the openings 111a. Although the delivery tube 122 can be coupled to the cover 105, in is contemplated that a delivery tube 122 can be coupled directly to the openings 111a. It is also contemplated that a nasal cannula having prongs incorporated therein can be coupled to any of the respiration sensor devices 110, 110a of the present disclosure.

Nasal inhalation flow passages 119a extend from the openings 111a. For example, nasal inhalation flow passages 119a may be enclosed conduits formed as part of the respiration sensor device 110 and having an arcuate shape configured to terminate in a position to provide fluid flow from the openings 111a to the subject's or patient's nares. The arcuate shape of the nasal inhalation flow passages 119a can be formed so that each conduit extends from an opening 111a of the housing toward the nasal inlet 113 of the nasal flow passage. An end portion of the nasal inhalation flow passages 119a, opposite relative to the housing 112, can include an opening positioned adjacent to the nasal inlet 113 of the respective nasal flow passage. In some embodiments of the present disclosure, each opening of the nasal inhalation flow passage 119b can define a plane that is parallel relative to a plane defined by the nasal inlet 113 of the nasal flow passage.

In some embodiments, the nasal inhalation flow passages 119a may be part of the nasal cannula assembly 120 and are inserted through the openings 111a to provide fluid flow from the delivery tubes 122 to the subject's or patient's nares.

In some aspects of the present disclosure, the nasal inhalation flow passages 119a comprise a first nasal inhalation flow passage extending in a first direction, and a second nasal inhalation flow passage extending in a second direction. The first and second directions can be parallel or transverse relative to each other. In some embodiments, the first and second directions are transverse relative to each other such that the first and second nasal inhalation flow passages can extend from the housing 112 in a directed toward each other. The direction of the nasal inhalation flow passages 119a toward each other can provide a flow of fluid toward the patient's septum or another portion of the patient's nose. When the flow of fluid is directed toward the patient's septum, a first area of the nare, proximal to the septum, can have a higher pressure relative to a second area of the nare. The second area of the nare can provide a path for exhalation having less resistance than the first area, thereby reducing the exhalation effort required by the patient.

Figure 14A:
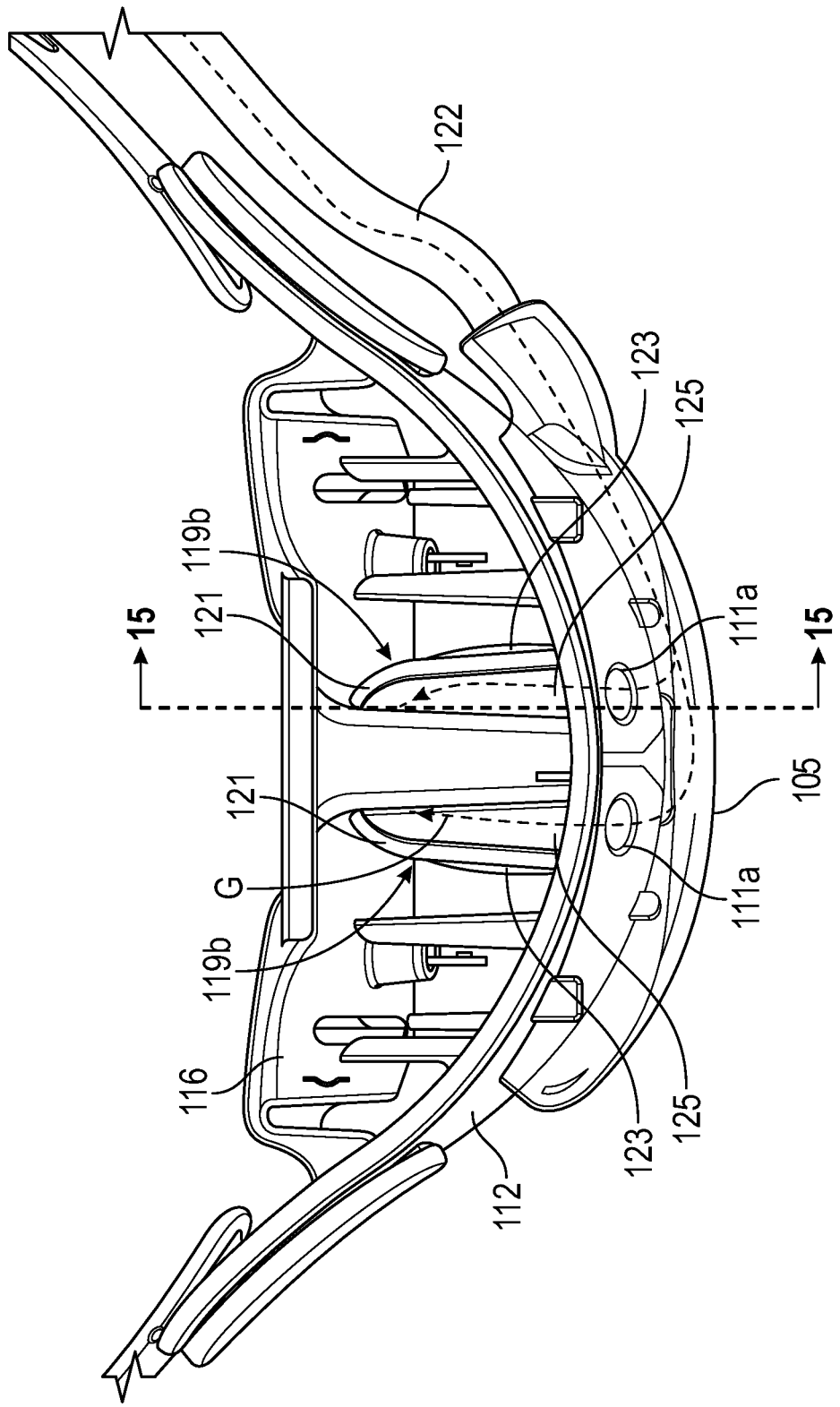
FIG. 14A illustrates a top view of a respiration sensor cannula device, according to some embodiments.
Figure 14B:
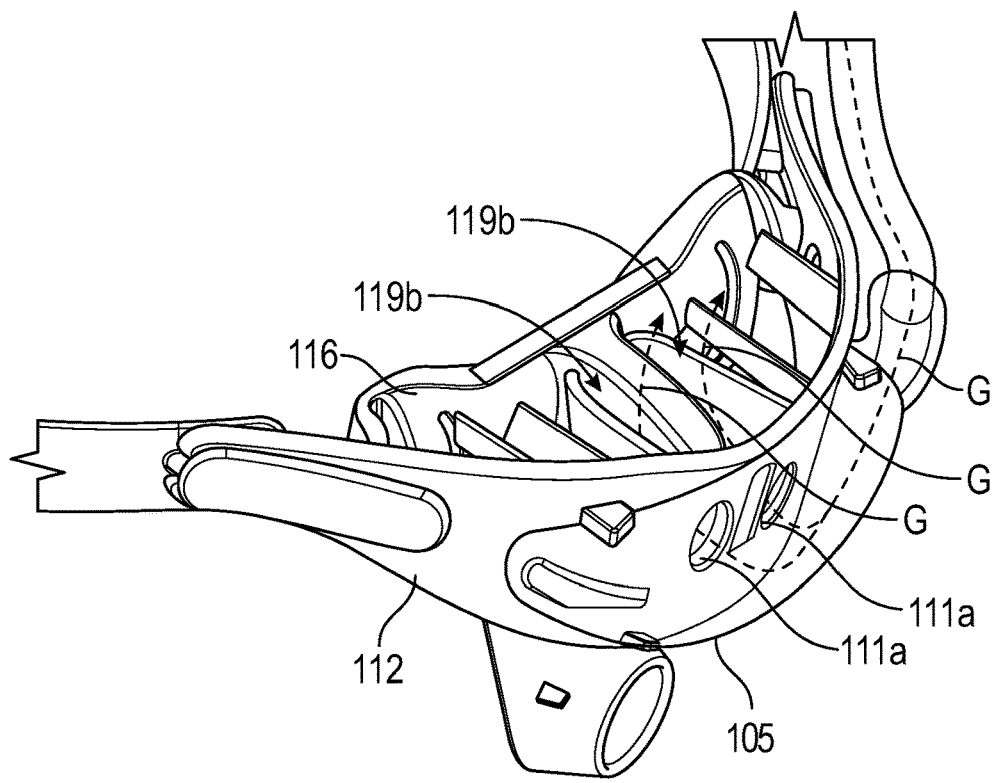
FIG. 14B illustrates a front perspective view of the respiration sensor cannula device of FIG. 14A.

In some embodiments of the present disclosure, such as those shown in FIGS. 14A and 14B, the nasal inhalation flow passages 119b of the respiration sensor device are shaped as a chute configured to direct a flow of gas from the opening 111a of the housing toward the patient's nares while creating an ambient environment of the gas for inhalation by the patient. The nasal inhalation flow passages 119b include an open top formed by a wall 121, whereby the wall 121 directs the gas toward the open top.

The wall 121 is positioned, at least in part, within each of the nasal flow passages 31. The wall 121 can have side portions 123 and a bottom portion 125 that extend from an inner surface of the housing 112 toward the shroud 116. The wall 121 can extend from the inner surface of the housing 112 to the shroud 116. In some embodiments of the present disclosure, the wall 121 extends from the inner surface of the housing 112 toward the shroud 116a a distance that is larger than a cross-sectional width of the opening 111a. In some embodiments, the wall 121 extends from the inner surface of the housing 112 toward the shroud 116a to form an elongate open top.

Figure 15:
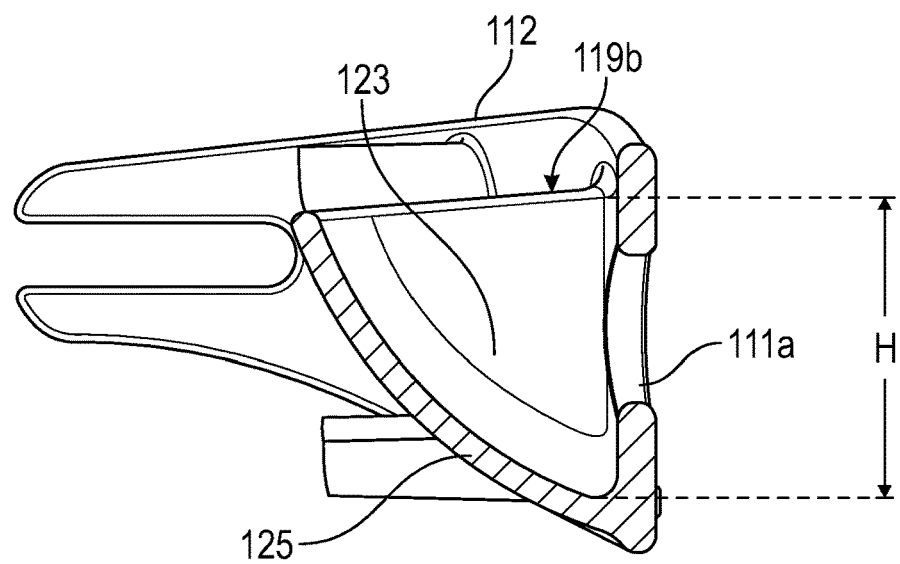
FIG. 15 illustrates a cross-sectional detail view of the respiration sensor mask device of FIG. 14A.

Referring to FIG. 15, which shows a cross-sectional view of the housing 112 of FIGS. 14A and 14B, the side portions 123 of the wall can have a height between the nasal inlet 113 and the nasal outlet 115 of the respiration sensor device. The height H of the side portions 123 of the wall can decrease from the housing 112 in a direction toward the shroud 116. The bottom portion 125 of the wall extends in a direction that is transverse relative to the side portions of the wall. Because the bottom portion 125 of the wall extends from the side portions 123 of the wall, the bottom portion 125 forms an inner surface of the nasal inhalation flow passages 119b that is inclined in a direction toward the nasal inlet 113 of the nasal flow passages. Thus, the inner surfaces of the wall 121 can direct a flow of gas from the opening 111a of the housing in a direction toward the nasal inlet 113.

In some embodiments of the present disclosure, a width between the inner surfaces of the nasal inhalation flow passages 119b tapers in a direction away from the housing 112. FIG. 14A shows the width between the inner surfaces of the nasal inhalation flow passages 119b decreasing from the housing 112 toward the shroud 116. In some aspects of the present disclosure the width of the nasal inhalation flow passages 119b results in a consistent velocity of the gas across the open top of the nasal inhalation flow passages 119b.

In some embodiments, a portion of the nasal inhalation flow passages 119b can be formed by housing 112. For example, a portion of the nasal inhalation flow passages 119b can be formed by a portion of the housing 112 extending between first and second side portions of the wall. The portion of the housing 112 between first and second side portions of the wall can be configured to retain a battery therein, such that the housing 112 separates first and second nasal inhalation flow passages 119b. In some embodiments of the present disclosure, a channel extends through the bottom portion of the wall and the portion of the housing 112 extends within the channel, between the side portions of the wall, to bisect the nasal inhalation flow passages 119b.

The open top of the nasal inhalation flow passages 119b define a cross-sectional area that is greater than a cross-sectional area defined by the openings 111a so a flow velocity of a gas can decrease as the gas moves from the openings 111a into the nasal inhalation flow passages 119b. The decrease in flow velocity can provide patient comfort, and the shape of the nasal inhalation flow passages 119b provides a large area where a patient's nares can receive the gas.

The direction of movement of a gas G is shown in broken lines in FIGS. 14A and 14B. In use, the gas can move from the delivery tubes 122, through the openings 111a, and into the nasal inhalation flow passages 119b where an ambient environment of oxygen is formed around the areas of the patient's nares. The ambient environment of oxygen can be comfortable for a patient because the gas is not directed toward the patient's nares at a velocity that may cause irritation and/or drying of the patient's skin and nasal passages.

In some embodiments, at least one nasal flow guide 117 is disposed proximate a nasal inlet 113 of each of the nasal flow passages 31 and at least one nasal flow guide 117 is disposed within each of the nasal flow passages 31. A nasal flow guide 117 can be positioned in a nasal flow passage 31, proximate any of the nasal inlet 113 and the nasal outlet 115. The nasal flow guide 117 is aligned relative to the nasal thermistor 41 or 42 to direct a flow of gas toward the nasal thermistor 41 or 42.

Features to attach the respiration sensor cannula device 100 can include any of a string, strap, or band, which can maintain a position of the respiration sensor cannula device 100 relative to the patient's physiognomy. For example, a strap 135, shown in FIG. 16, can have ends that are attached to the respiration sensor device 110 to form a loop. The ends of the strap 135 can couple to any of the housing 112, the base 114, the shroud 116, and the cover 105. The strap 135 can have a length such that the respiration sensor device 110 is engaged against a patient's face when the device is worn by the patient. In some embodiments, an additional (e.g., second) strap 137 extends from any of the strap 135 or the respiration sensor device 110. The additional strap 137 can provide additional support and tension to secure the respiration sensor cannula device 100 with the patient. The strap 135 and additional strap 137 can be configured such that a portion of the strap 135 extends above a patient's ears, and a portion of the additional strap 137 extends below a patient's ears.

Figure 16:
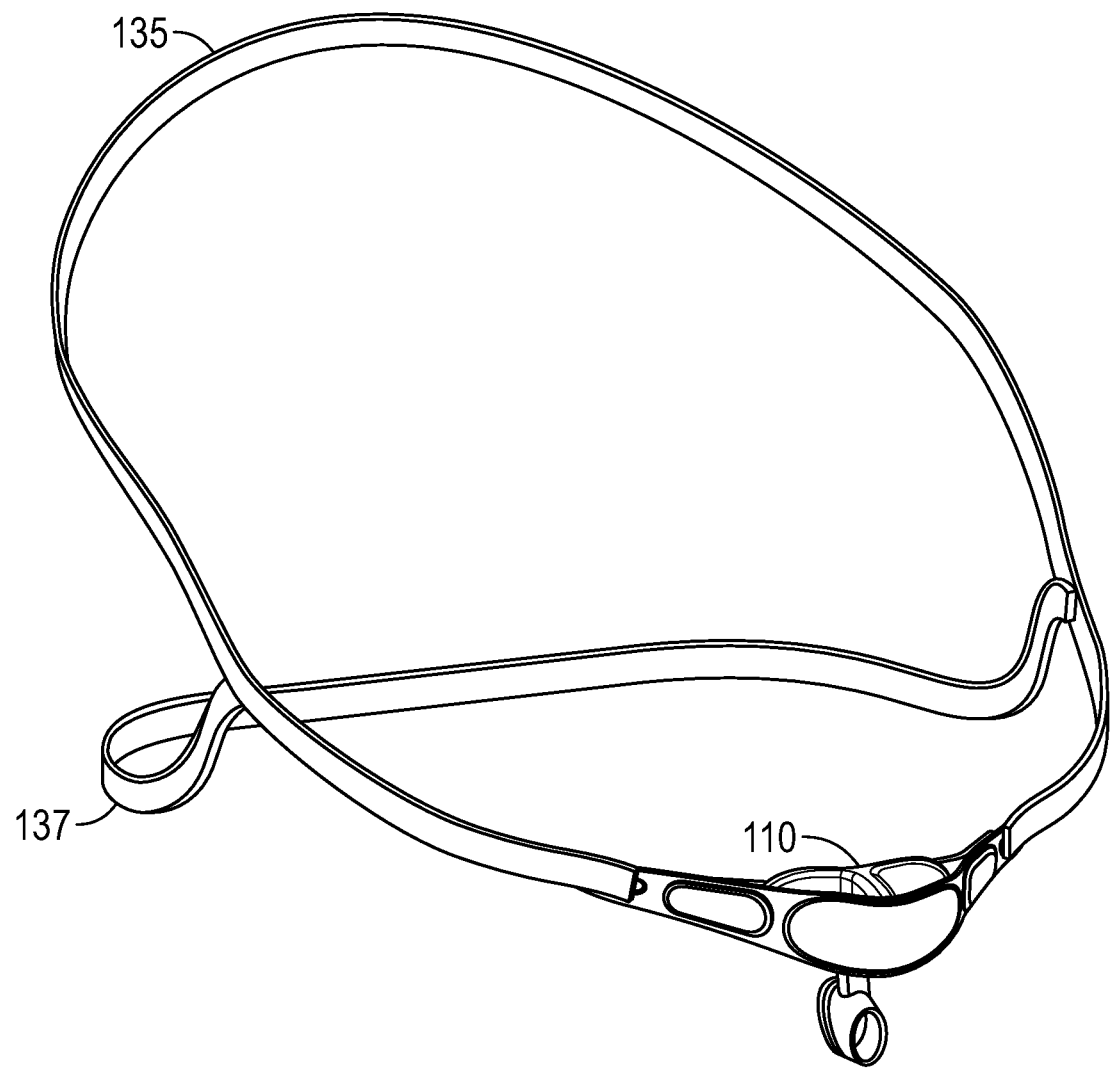
FIG. 16 illustrates a front perspective view of a respiration sensor device having a strap, according to some embodiments.
Figure 17:
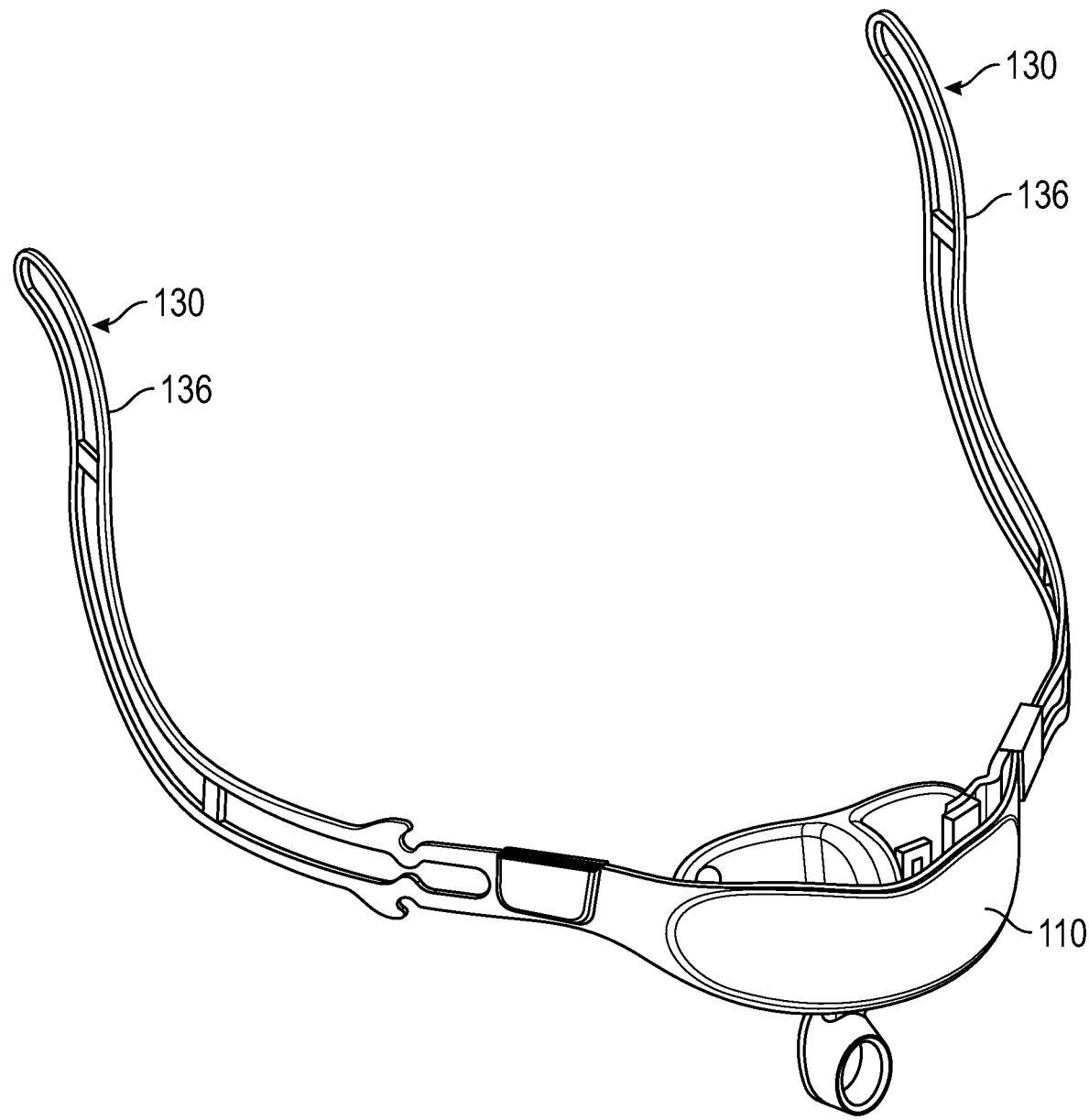
FIG. 17 illustrates a front perspective view of a respiration sensor device having a band, according to some embodiments.

As another example, a placement band 130, shown in FIG. 16, may be coupled or integrally formed with the respiration sensor device 110. The placement band 130 includes straps 136 for engagement with the patient's face. The straps 136 are shaped to follow a contour of a patient's face. When the placement band 130 is used with a patient, the straps 136 extend from the respiration sensor device 110 below the cheek bone, in front of the ear, and then over the ear toward the posterior of the patient's head. The straps 136 can extend around the patient's head and couple together. The straps can extend around the patient's head and be unitarily formed. In some embodiments, a flexible band extends between the straps 136. As shown in FIGS. 7A-13, the placement band 130 may couple or integrate with the respiration sensor device 110 via an engagement pad 132a.

The engagement pad 132a can include a proximal portion coupled to the base 114, and a distal tip portion extending from the proximal portion. The proximal portion can form a standoff 131 and the distal portion can form a barb 133. The standoff that extends between the base 114 and the barb 133. The engagement pad 132a extends away from a surface of the base 114 in a first direction. The standoff 131 can have a cross-sectional width, transverse to the first direction, that is less than a width of the barb 133. The placement band 130 can be coupled to any of the base 114 and the engagement pad 132a. In some embodiments, the engagement pad 132a is positioned between the base 114 and the placement band 130. In some embodiments, the placement band 130 is coupled to the barb 133.

In some embodiments, the placement band 130 has a semi-rigid framework that is configured to guide additional straps that overlay the placement band 130 and extend over preferred placement portions of a patient's face. In some embodiments, the placement band 130 is a flexible plastic material that is configured to substantially retain its shape during use. The flexible placement band 130 can move, in a first plane, towards or away from a patient's face. The placement band 130 can be moved or biased in the first plane to engage against the patient's face and adapt to the shape of the patient's face. The placement band 130 is less flexible relative to a second plane, transverse to the first plane, thereby preventing or resisting movement of the placement band 130 along the patient's face or twisting of the placement band 130.

The placement band 130 can have a width that is approximately 5 mm, but it can be wider or narrower. A wider band can reduce the surface pressure on the face by the band. At least a portion of a surface of the placement band 130 can be covered with a material that is soft and/or breathable. For example, a surface of the placement band 130 configured to engage against the face or skin of the patient can include a cotton or similar material.

The shape of the placement band 130 is configured to extend from the respiration sensor device 110, below the cheek bones of the patient. The placement band 130 can curve from the area below the cheek bones of the patient toward the patient's ears, forming a shape of an S-curve or similar.

The placement band 130 can be coupled with an additional band and/or strap that pulls the placement band 130 and respiration sensor device 110 towards the patient's face, such that a force vector of the respiration sensor device 110 is approximately straight, towards the face or upper lip of the patient. Accordingly, the placement band 130 can decrease the surface pressure against the patient's isthmus or other portions of the patient's face or lip.

Figure 8A:
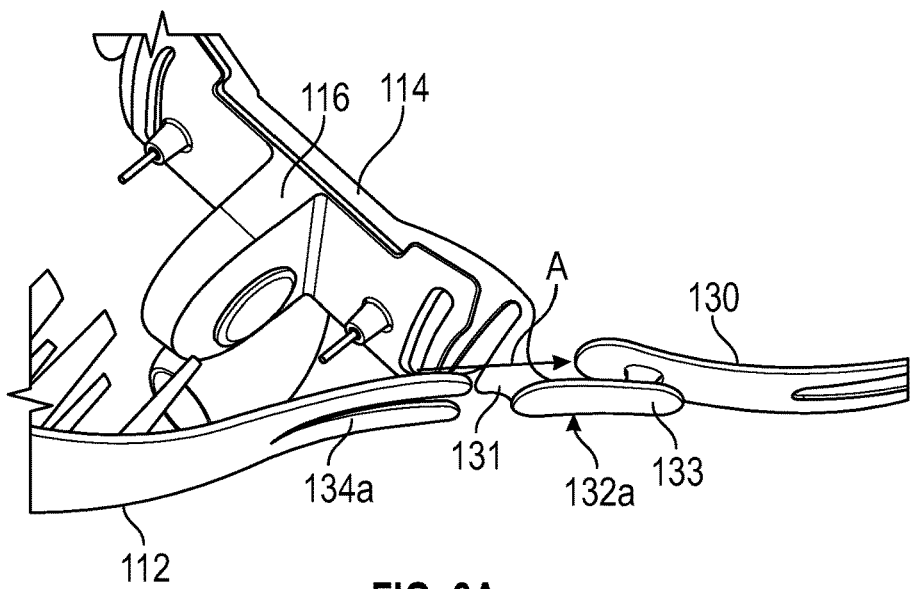
FIGS. 8A and 8B illustrate top perspective views of a respiration sensor device, according to some embodiments.
Figure 8B:
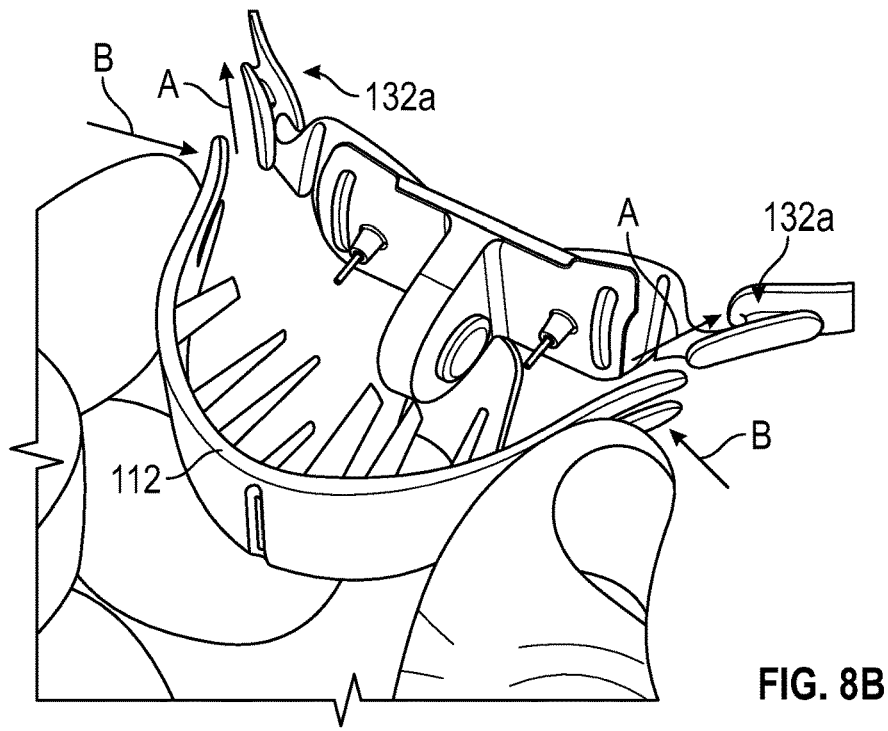

Referring to FIGS. 8A and 8B, the housing 112 can be coupled to the base 114 by slideably engaging a slot 134a in the housing 112 with the engagement pad 132a. The slot 134a can have a width that is greater than a width of the standoff 131 and less than a width of the barb 133. When the housing slot 134a is slideably engaged with the standoff 131, the housing is retained between the base 114 and the barb 133.

To couple the housing 112 to the base 114, the housing 112 is moved toward the base so that a portion of the housing 112 having the slot 134a moves in the direction of arrow A (FIGS. 8A and 8B), toward the engagement pad 132a. The housing can be flexible to provide an interference fit between the housing 112 and the base 114 when coupled together. To couple the housing 112 to the base 114, lateral end portions of the housing 112 are biased toward each other, in the direction of arrow B (FIG. 8B). When the lateral end portions of the housing 112 are biased toward each other, the portions of the housing 112 having the slot 134a align with the standoff 131 of each engagement pad 132a. The housing 112 can then be moved in the direction of arrow A to engage the slots 134a with the engagement pads 132a. When the housing is released, thereby permitting the housing 112 to return to a neutral or unbiased configuration, the portions of the housing 112 having the slot 134a engage against the engagement pads 132a.

The cover 105 can coupled with any of the housing 112 and base 114 in a manner similar to the housing 112. The cover 105 can include engagement regions 106 configured to be engaged by a user to bias the cover portion 105. The engagement regions 10 can be located at left and right lateral portions of the cover 105 so that when the cover 105 is biased, the engagement regions 106 move toward each other. In some embodiments, when the cover 105 is biased, the housing 112 is also biased. In some embodiments, the cover 105 comprises left and right lateral portions 106 comprising a slot configured to couple with the engagement pad 132a. In some aspects of the present disclosure any of a top and bottom edge of the cover 105 can clip onto the top and bottom edge of the housing 112, respectively.

Figure 9:
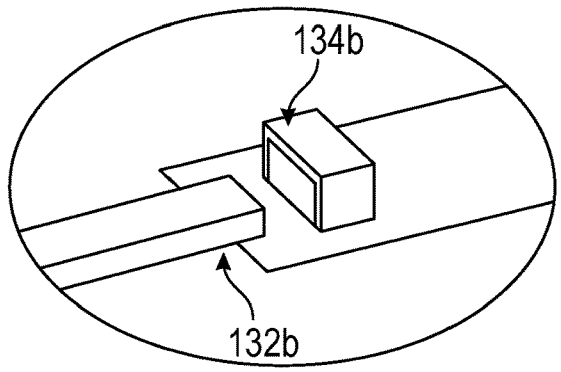
FIG. 9 illustrates an alternative embodiment of a coupling between portions of the respiration sensor device.

It should be understood that additional or different engagement mechanisms are contemplated for coupling any of the housing 112, the base 114, or the cover 105 together. In some embodiments, the base can comprise a slot and the housing can comprise a standoff or protrusion configured to be inserted with the slot of the base 114. In some embodiments, the housing 112 can be made from a flexible material and comprise a slot or aperture extending therethrough. The slot can comprise a width or diameter that is less than a width of the engagement pad 132a. To couple the housing 112 and the base 114, the housing can be biased or stretched over the engagement pad 132a and around the standoff. Referring to FIG. 9, in some embodiments, any of the base, housing, and cover can comprise a passage 134b, and the other of the base, housing, and cover can have a projection 132b configured to be received into the passage 134b. In some aspects of the present disclosure, the projection 132b can include a barb configured to engage the portion of the base, housing, or cover forming the passage 134b to resist separation of the projection 132b from the passage 134b.

The engagement pad 132a can comprise an outer surface configured to engage against a fluid delivery tube 122. The engagement pad 132a can provide a resting and/or mating surface for receiving the end portion of the delivery tube 122. One or more delivery tube 122 can be separately coupled to the respiration sensor device 110 or can be a portion of the nasal cannula assembly 120.

A distal end portion of the engagement pad 132a can have a concave outer surface configured to engage against the delivery tube 122. The shape of a portion of the engagement pad 132a or the concave surface can be configured to align the delivery tube 122 relative to a portion of the respiration sensor cannula device 100. When coupled with the respiration sensor cannula device 100, the end portion of the delivery tube 122 extends across the engagement pad 132a and is positioned between the housing 112 and the cover 105. The delivery tube 122 is coupled with the respiration sensor cannula device 100 by engagement of the end portion of the delivery tube 122 between the housing 112 and the cover 105. In some embodiments, the engagement pad 132a can include any of a groove, channel, and/or clip configured to retain a portion of the delivery tube 122 therein. For example, the delivery tube 122 can coupled with the respiration sensor device 110 by an interference fit between the delivery tube 122 and the engagement pad 132a.

In some embodiments, the outer surface of the housing 112 may include a spacer passage 118a configured to receive a battery spacer (not shown) therethrough. The battery spacer (e.g., strip or tape) may be pulled out through spacer passage 118a when the respiration sensor device 110 is to be used, thus allowing a battery and a circuit contact within the respiration sensor device 110 to establish an electrical connection. Accordingly, after removal of the battery spacer through the spacer passage 118a, the nasal cannula assembly 120 may be coupled to the respiration sensor device 110. For example, the cover 105 may be part of the nasal cannula assembly 120 and connected to the delivery tubes 122, such that the cover 105 and delivery tubes 122 may be placed into position on the housing 112 after removal of the battery spacer. As another example, the cover 105 may be part of the respiration sensor device 110, where the cover 105 is removed to allow access to the battery spacer and then replaced back in to position over the end portions of the delivery tubes 122. In some embodiments, the cover 105 includes a passage to permit removal of the battery spacer after the cover 105 is placed into position on the housing 112. The passage through the cover 105 can be formed as a sleeve or tunnel to permit the battery spacer to be removed while retaining a fluid or gas between the housing 112 and the cover 105

In some embodiments, the spacer passage 118b extends through a top portion of the housing 112. For example the spacer passage 118b can extend along a plane that is parallel to a plane defined by the top of the electronics board. The spacer passage 118b permits the battery space to be removed before or after the cover 105 is placed into position on the housing 112.

Figure 18A:
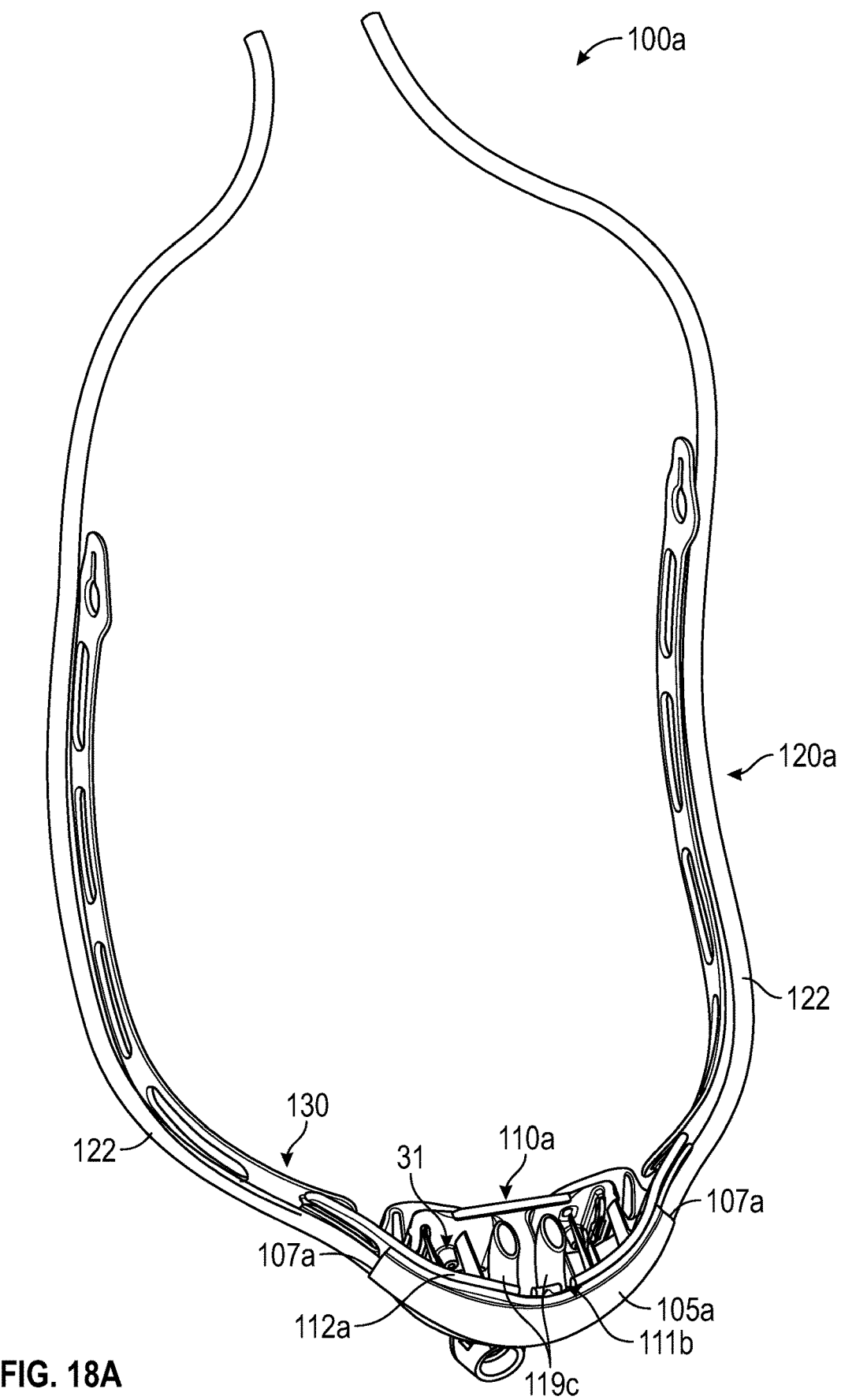
FIG. 18A illustrates a front perspective view of a respiration sensor cannula device, according to some embodiments.
Figure 18B:
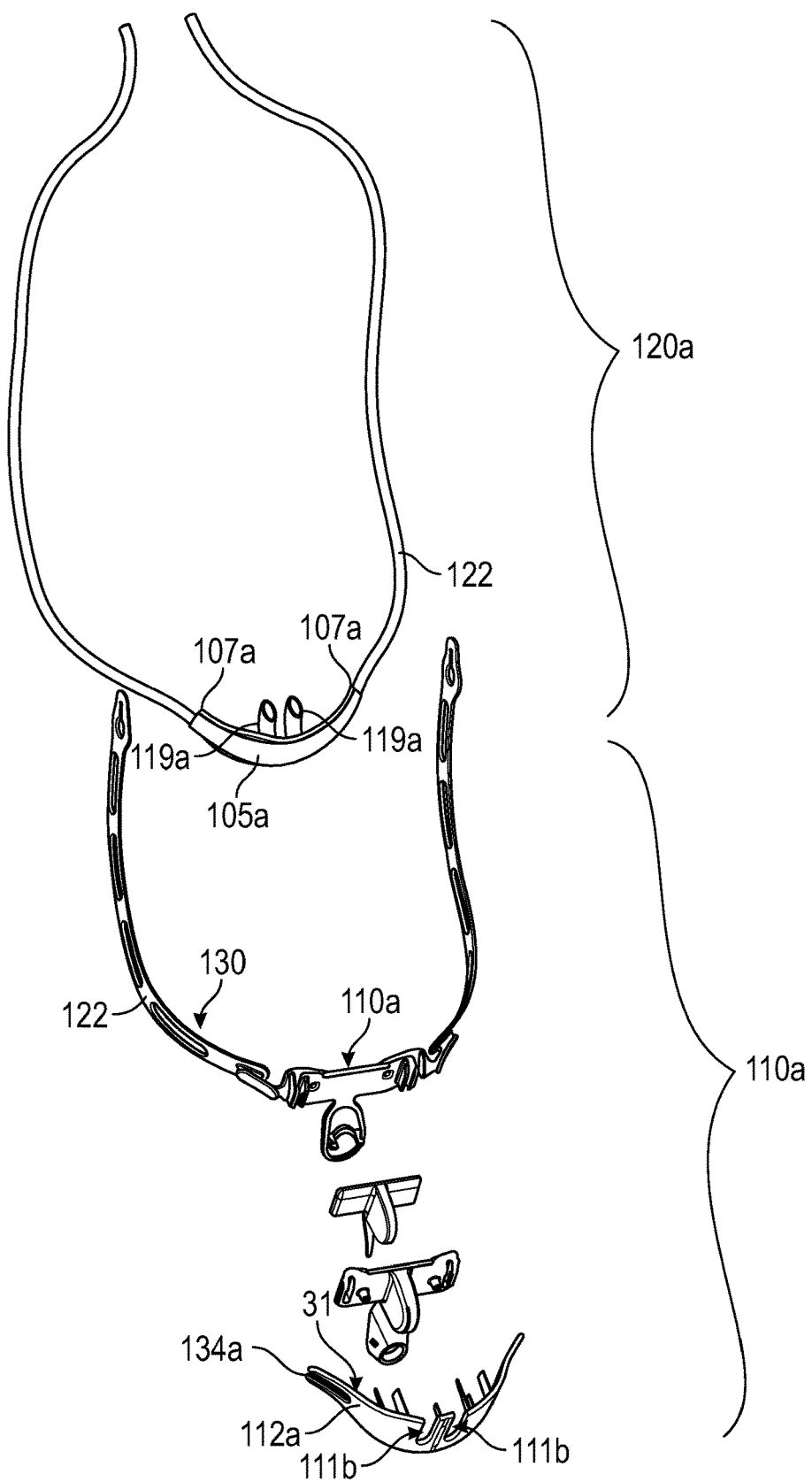
FIG. 18B is an exploded view of FIG. 18A.
Figure 19:
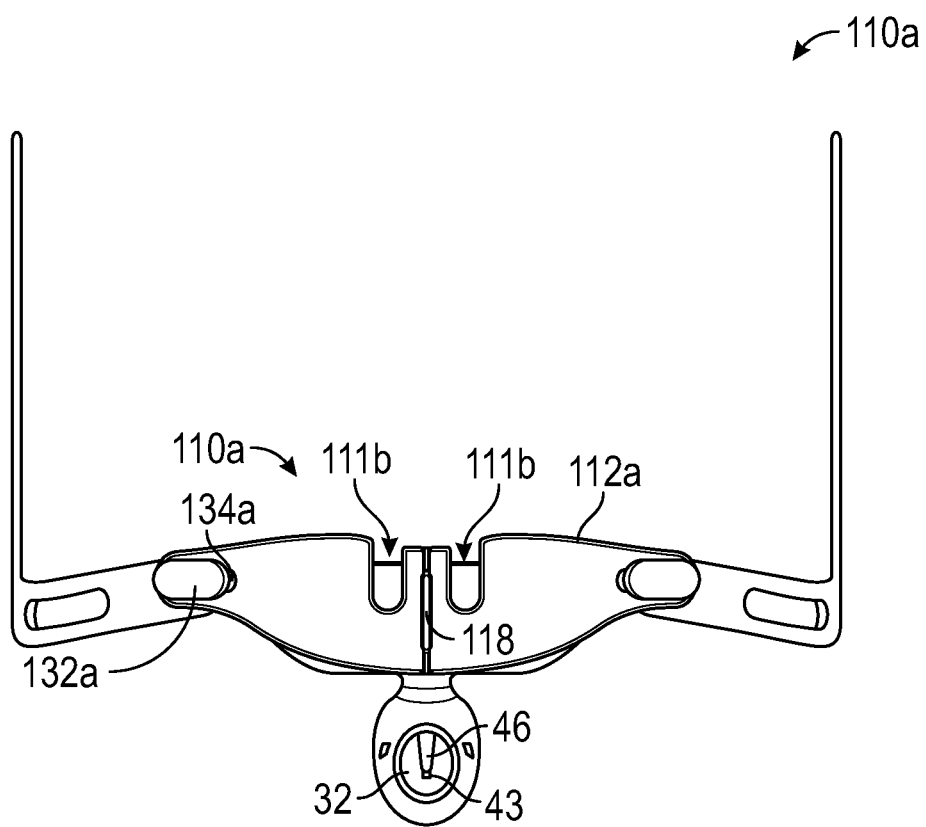
FIG. 19 illustrates a front plan view of the respiration sensor cannula device of FIG. 14A with the nasal cannula removed.

FIGS. 18A-19 illustrate a respiration sensor cannula device 100a having a respiration sensor device 110a and a nasal cannula assembly 120a. Respiration sensor cannula device 100a has many features in common with respiration sensor cannula device 100 and the reference numbers of the common features remain the same for simplicity. As shown by FIGS. 18 and 19, the respiration sensor device 110a has a housing 112a that includes open slots 111b. Open slots 111b are configured to receive nasal inhalation flow passages 119c, which are part of the nasal cannula assembly 120a. Here, the nasal cannula assembly 120a includes delivery tubes 122 that connect at inlet ports (e.g., tube openings) 107a of a fluid delivery cavity 105a. The nasal inhalation flow passages 119c (e.g., nasal prongs) protrude out from the fluid delivery cavity 105a and are removably received by the open slots 111b. Thus, fluid flows through the delivery tubes 122 into the fluid delivery cavity 105a, then out through the nasal prongs 119c and into the patient's nares during use.

FIGS. 20-25 illustrate a respiration sensor mask device 200 having a respiration sensor device 210, a respiration mask assembly 220, and a mask connection band 250.

In some embodiments, at least a portion of the respiration sensor device 110, 110a, 210 can remain worn by the patient while any of a nasal cannula assembly 120, 120a or a respiration mask assembly 220 is interchangeably coupled to the respiration sensor device 110, 110a, 210. In some embodiments, a nasal cannula assembly 120, 120a and a respiration mask assembly 220 can be coupled to the respiration sensor device 110 at the same time.

The respiration sensor device 110, 110a, 210 can include an attachment mechanism, including any of an engagement pad 132a, slot 134a, or other mechanism configured to permit coupling with the nasal cannula assembly 120, 120a and/or respiration mask assembly 220. The respiration sensor device 110, 110a, 210 can be worn by the patient, and any of the nasal cannula assembly 120, 120a and/or respiration mask assembly 220 can be coupled to the respiration sensor device 110, 110a, 210 with the attachment mechanism. For example, while the respiration sensor device 110, 110a, 210 is worn by the patient, any of the nasal cannula assembly 120, 120a or respiration mask assembly 220 can be removed while leaving the housing 112, 112a, 212 affixed to the respiration sensor device 110, 110a, 210. Then, another nasal cannula assembly 120, 120a or respiration mask assembly 220 can be coupled to the respiration sensor device 110, 110a, 210 by engaging the attachment mechanism therebetween.

The respiration mask assembly 220 can be coupled with a respiration sensor device 110, 110a, 210 using an attachment mechanism, such the engagement pad 132a and/or slot 134a. In some embodiments, the respiration mask assembly 220 can be coupled with a respiration sensor device 110, 110a, 210 with a mask connection band 250a, 250a in addition to the attachment mechanism or in place of the attachment mechanism.

The mask connection band 250 includes a retaining band 252, connection members 254 and support members 256. The retaining band 252 is configured to engage and/or retain the respiration mask assembly 220 to the respiration sensor device 210. The connection members 254 and support members 256 are configured to engage with the respiration mask assembly 220 and with the respiration sensor device 210. For example, connection member slots 255 of the connection members 254 may mate or otherwise removably engage with housing slots 211 of housing 212 of the respiration sensor device 210, thereby coupling the mask connection band 250 to the respiration sensor device 210. As another example, engagement surfaces 257 of the support members 256 may engage with a portion of the respiration sensor device 210, such as the engagement pad 132a, thereby providing stability to the respiration sensor mask device 200 and reducing movement of the respiration mask assembly 220 relative to the respiration sensor device 210 and/or to the patient's face.

Figure 22:
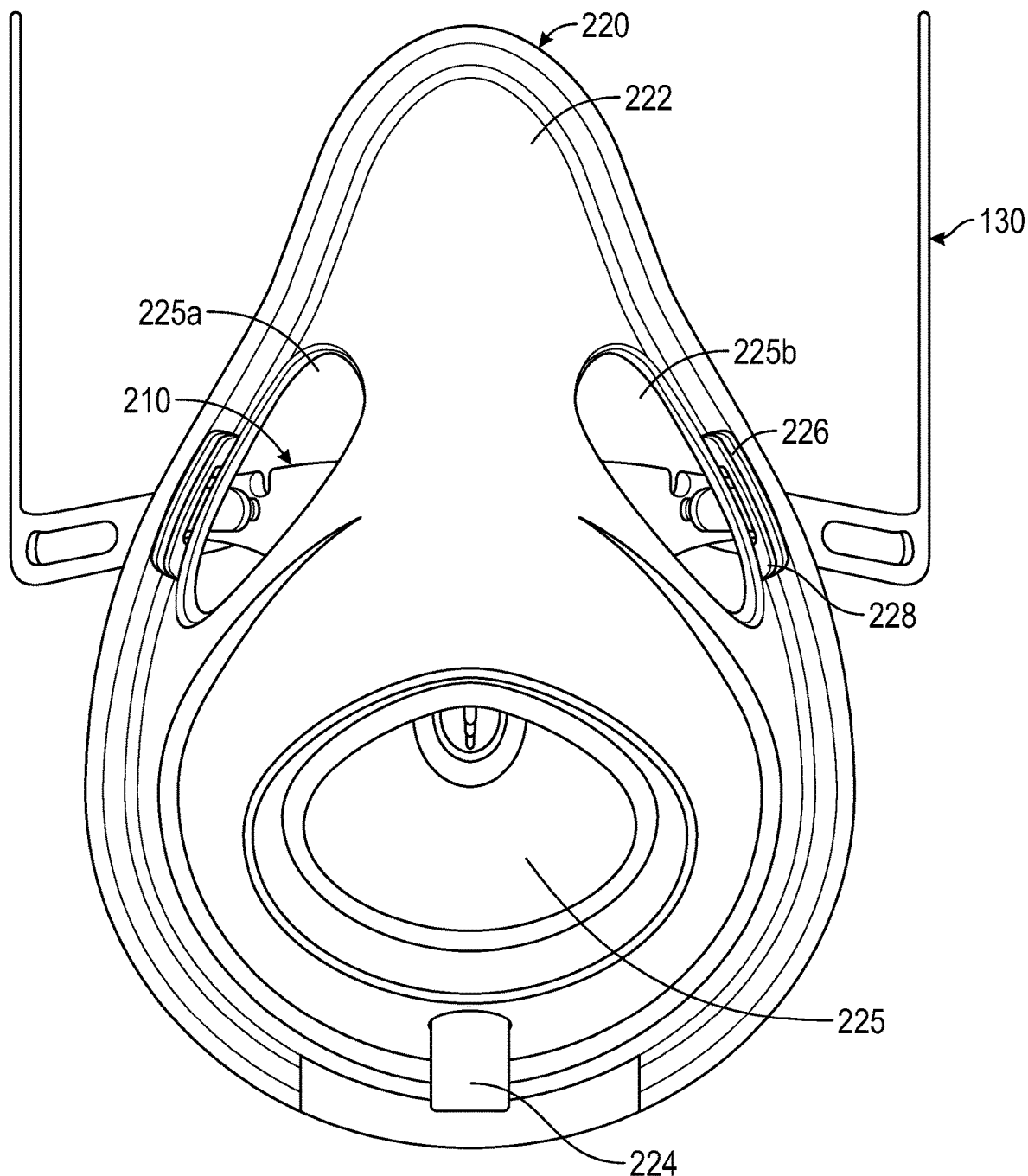
FIG. 22 illustrates a front plan view of the respiration sensor mask device of FIG. 20 with the connection band removed.

The respiration mask assembly 220 includes a mask 222, a fluid port 224, connection member openings 226 and support member openings 228, as illustrated in FIG. 22. Fluid (e.g., oxygen, nitrous oxide) is delivered to the fluid port 224 and the fluid is then dispersed into an interior volume of the mask 222, thereby placing the fluid in communication with the patient's nares and mouth during use when the respiration sensor mask device 200 is affixed to the patient's face. The connection members 254 and the support members 256 of the mask connection band 250 extend through the connection member openings 226 and the support member openings 228, respectively. Thus, the respiration mask assembly 220 is coupled and stabilized to the respiration sensor device 210, providing for the respiration sensor mask device 200 to be placed on, repositioned or removed from the patient's face as a unitary assembly.

The respiration mask assembly 220 may include a vent or opening to provide access to interior volume of the mask. The openings can also allow for exhaled gases such as carbon dioxide to be cleared from the patient cavity of the interior volume of the mask, reducing the incidence of carbon dioxide rebreathing. For example, the respiration mask assembly 220 shown in FIG. 22 includes three vent openings 225a, 225b, 225c. Two upper vent openings 225a, 225b are positioned to be adjacent to a patient's nose when the respiration mask assembly 220 is worn by the patient. The upper vent openings 225a, 225b can be laterally spaced apart on either side of the patient's nose when the respiration mask assembly 220 is worn. A lower vent opening 225c is positioned to be adjacent to a patient's mouth when the respiration mask assembly 220 is worn by the patient.

Figure 23:
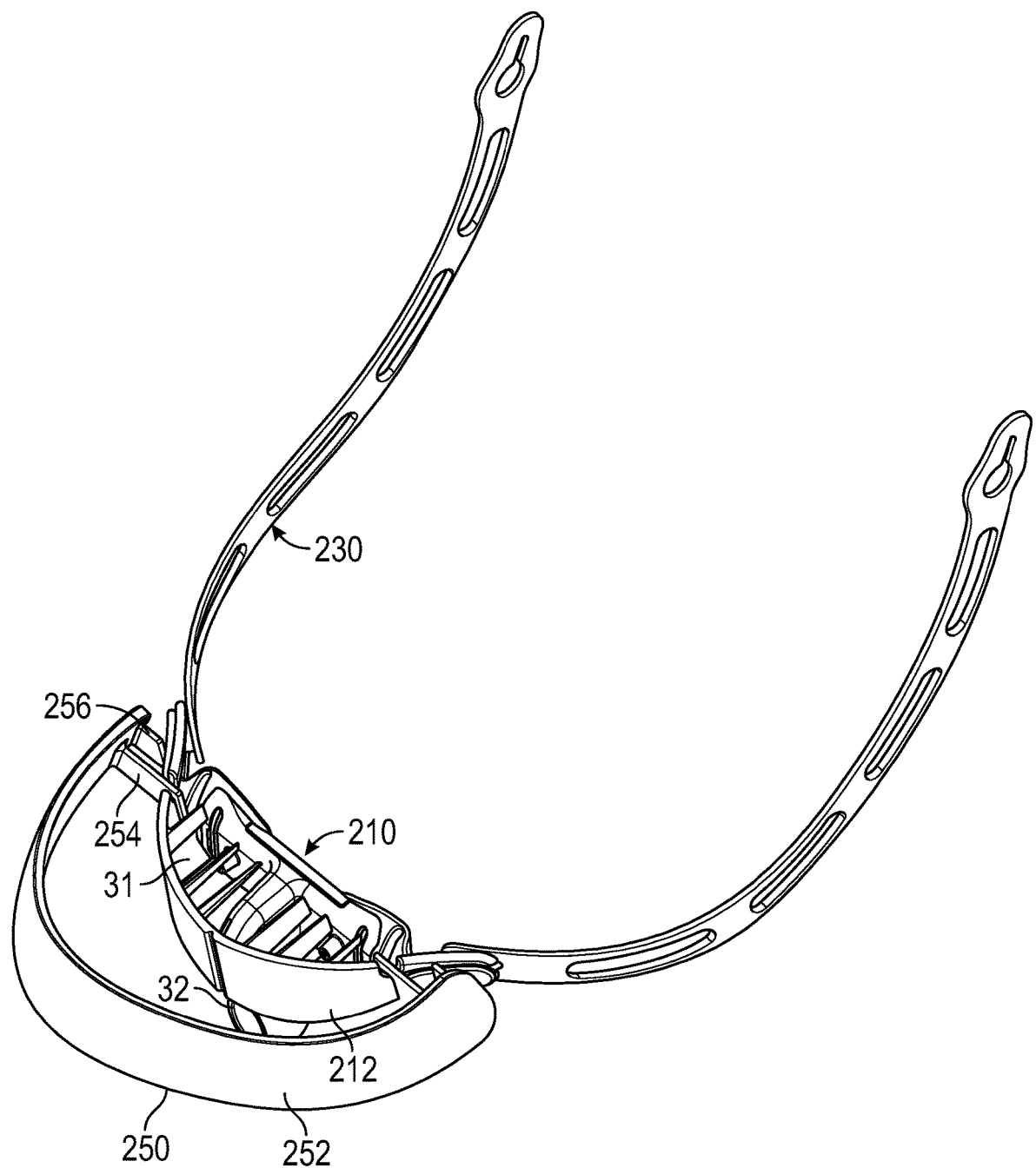
FIG. 23 illustrates a front perspective view of the respiration sensor mask device of FIG. 20 with the mask removed.
Figure 24:
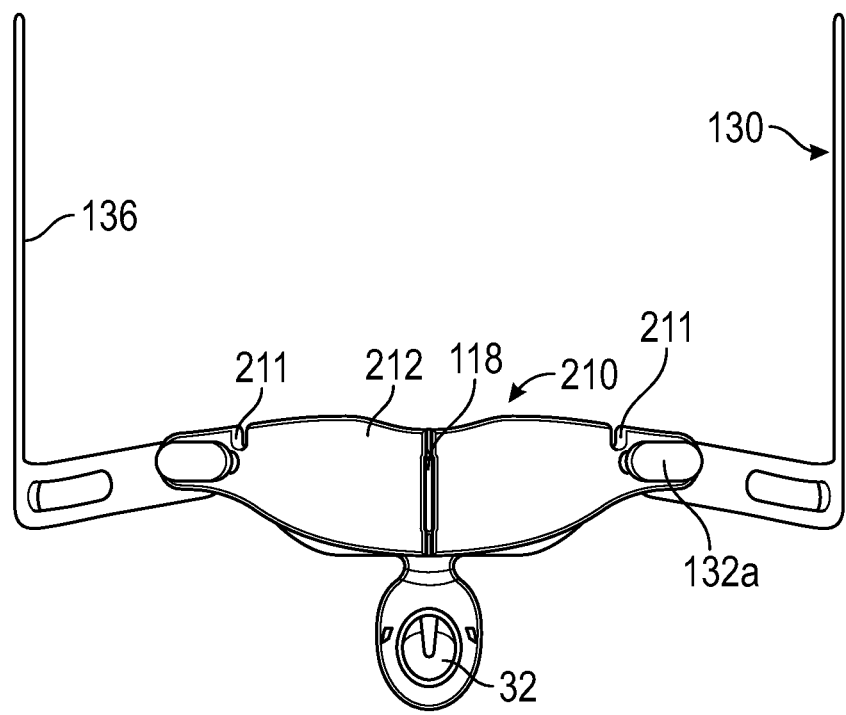
FIG. 24 illustrates a front perspective view of a respiration sensor device having a band, according to some embodiments.
Figure 25:
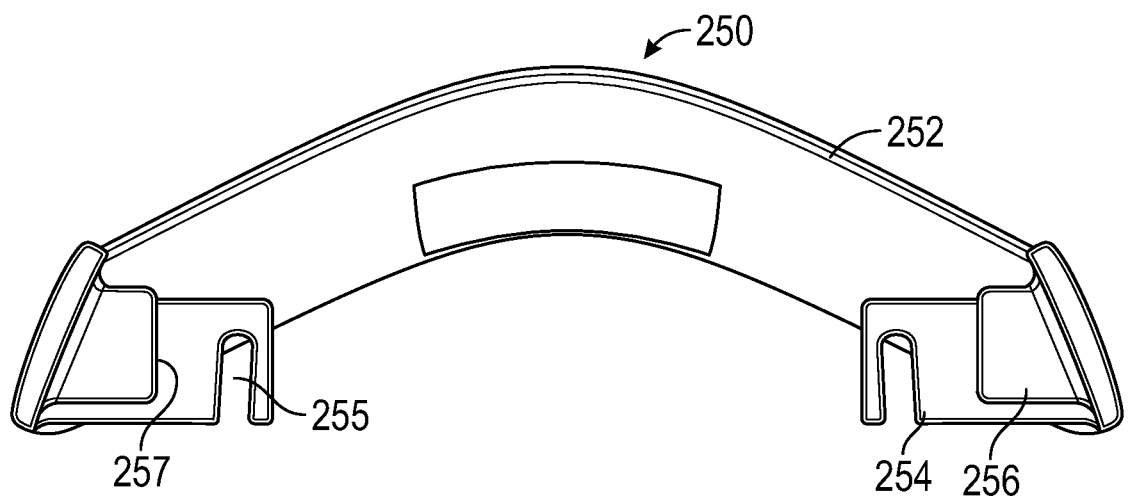
FIG. 25 illustrates a rear plan view of a connection band, according to some embodiments.

Respiration sensor device 210 has many features in common with respiration sensor devices 110, 110a and the reference numbers of the common features remain the same for simplicity. As shown by FIGS. 23 and 24, the respiration sensor device 210 has a housing 212 that includes housing slots 211 for receiving the connection members 254 of the mask connection band 250. Since the fluid delivery is provided by the respiration mask assembly 220 instead of a nasal cannula assembly 120, 120a, the housing 212 does not include openings 111a or open slots 111b as there are no nasal inhalation flow passages 119a, 119c to be received.

However, any of the features described above may be combined in various embodiments. For example, in some embodiments the respiration sensor device 110, 110a may be modified to include housing slots 211. This is particularly advantageous as it provides interchangeability of the modified respiration sensor device 110, 110a between respiration sensor cannula device 100, 100a and respiration sensor mask device 200. For example, a patient may need fluid delivery provided by a mask at certain times (e.g., patient bedbound, patient unconscious or sedated) for which a respiration sensor mask device 200 having the modified respiration sensor device 110, 110a may be used on the patient. At other times (e.g., patient awake and desiring comfort, patient mobile) it may be desirable for the patient to use a respiration sensor cannula device 100, 100a. Accordingly, the respiration sensor device 110, 110a may remain in position on the patient's face while the respiration mask assembly 220 is uncoupled and replaced by the nasal cannula assembly 120, 120a, or vice versa.

Figure 26:
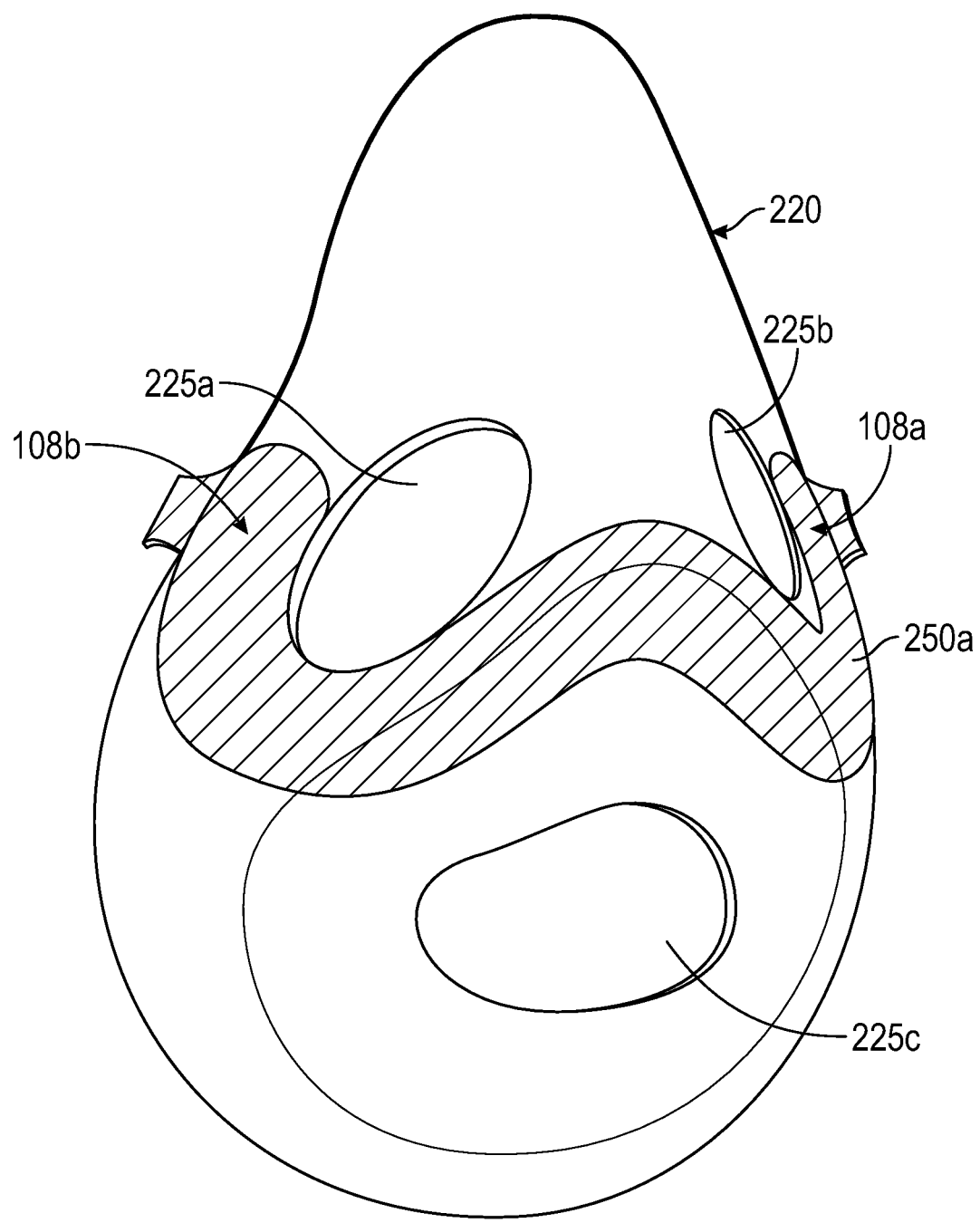
FIG. 26 illustrates a front perspective view of a respiration sensor mask device, according to some embodiments.

The mask connection band 250a may be sized and shaped as desired. For example, as shown in FIG. 26, a mask connection band 250a may be contoured to avoid blocking a portion or all of any of the nasal or oral vents 225a, 225b, 225c. The mask connection band 250a extends from a left lateral portion 108a and a right lateral portion 108b. To avoid blocking a portion or all of any of the nasal or oral vents 225a, 225b, 225c, the mask connection band 250a extends along a corresponding region of the mask 220 that is between the nasal vents 225a, 225b and the oral vent 225c.

In some aspects, the left and right lateral portion 108a, 108b are configured to be engaged by a user to bias the mask connection band 250a. When the left and right lateral portion 108a, 108b are biased toward each other, the mask connection band 250a can be coupled or detached with the housing 112. In some aspects, the mask connection band 250a includes slots configured to couple with a portion of the respiration sensor device 210 such as the engagement pad 132a. Different sizes and shapes of mask connection bands 250 may be used to affix different sized/shaped masks to the same respiration sensor device 210.

Figure 20:
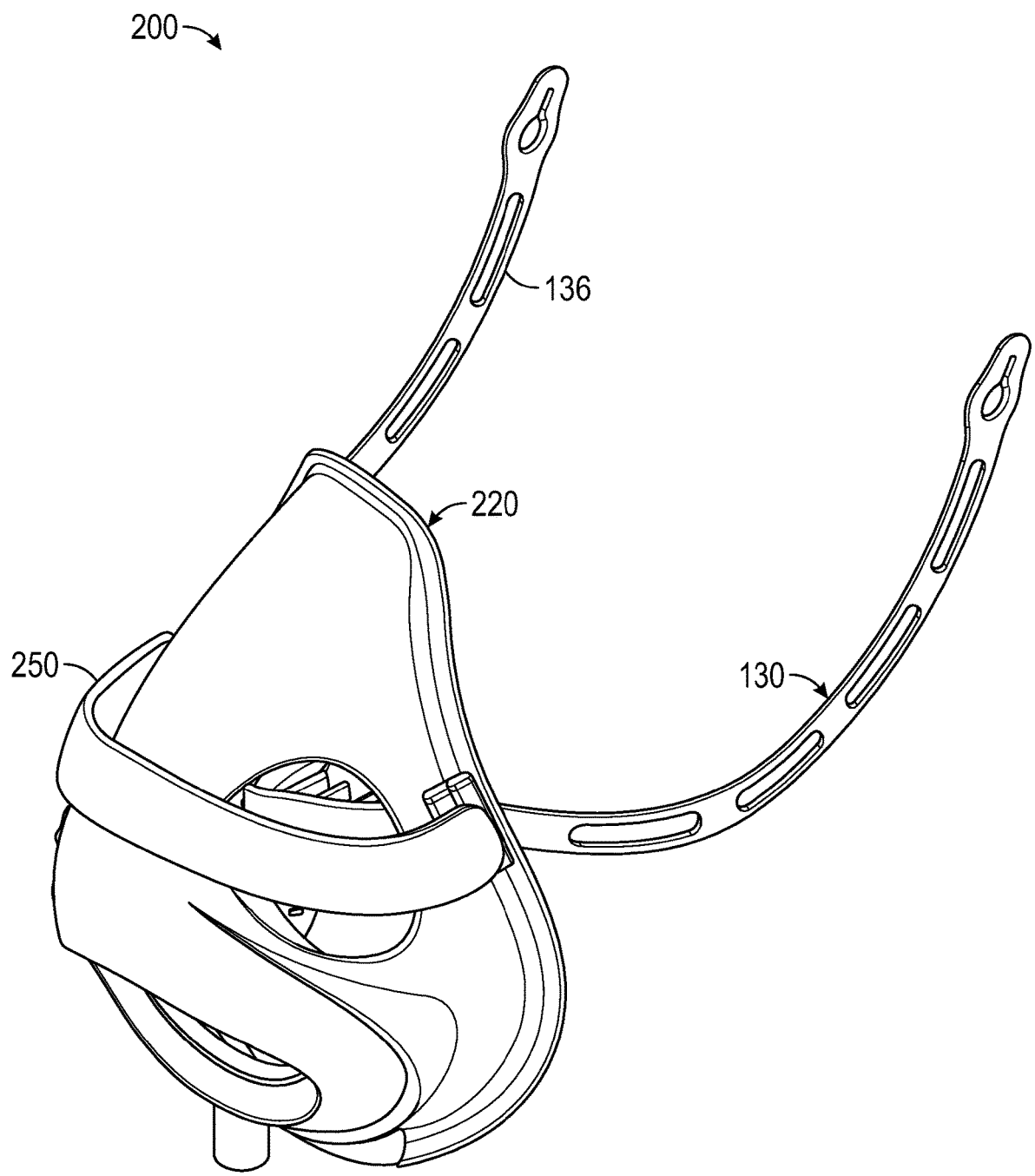
FIG. 20 illustrates a front perspective view of a respiration sensor mask device, according to some embodiments.
Figure 21:
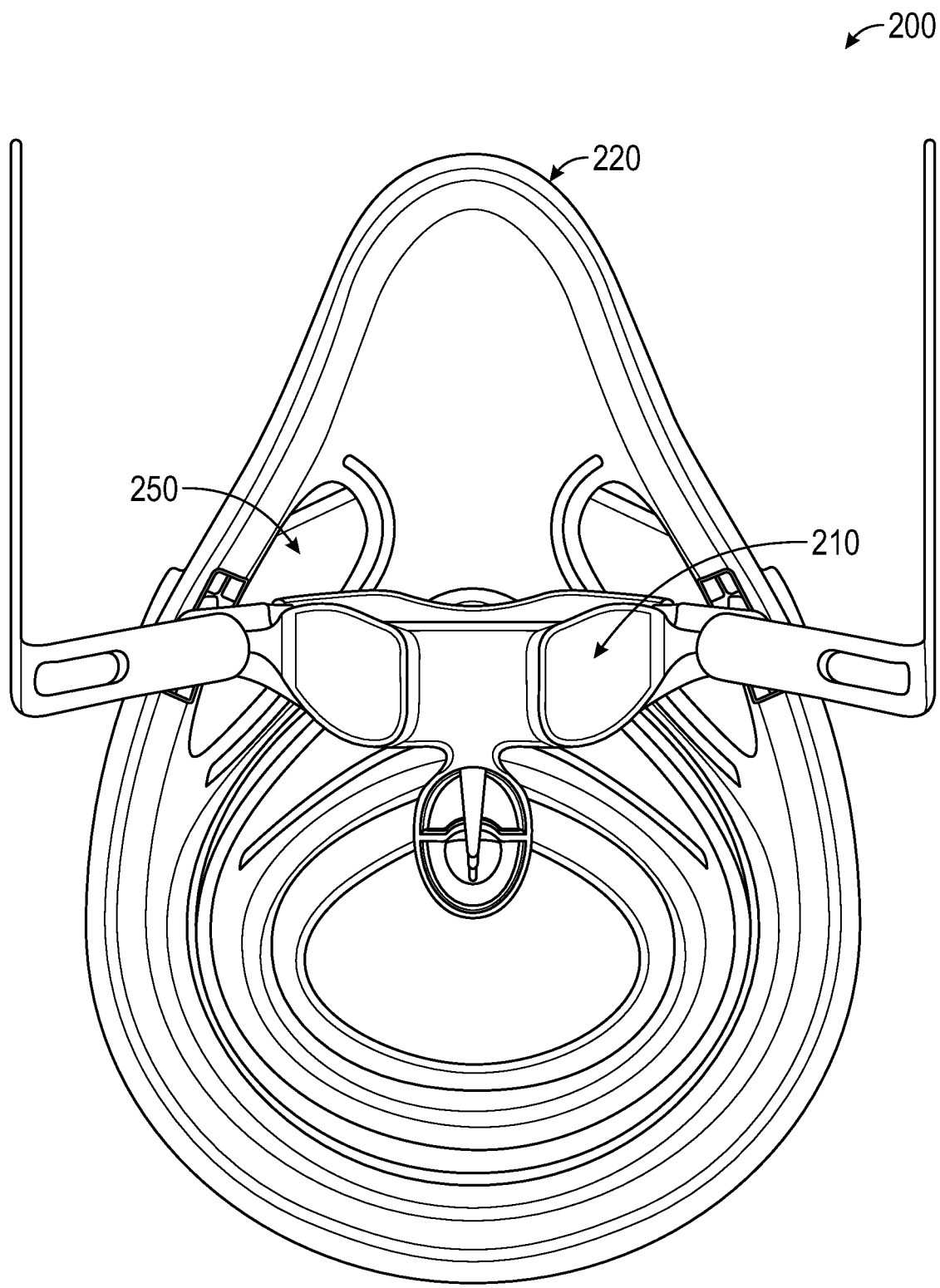
FIG. 21 illustrates a rear plan view of the respiration sensor mask device of FIG. 20.

When the respiration sensor device 210 is coupled with the respiration mask assembly 220, as shown in FIGS. 20 and 21, a fluid can be provided into the interior volume of the mask 222 without impeding operation of the respiration sensor device 210, and without impeding desired operation of the respiration mask assembly 220. In some embodiments, the respiration mask assembly 220 can provide a fluid into the interior volume of the mask 222, and can receive a sample of a fluid from within the interior volume of the mask 222.

Figure 27:
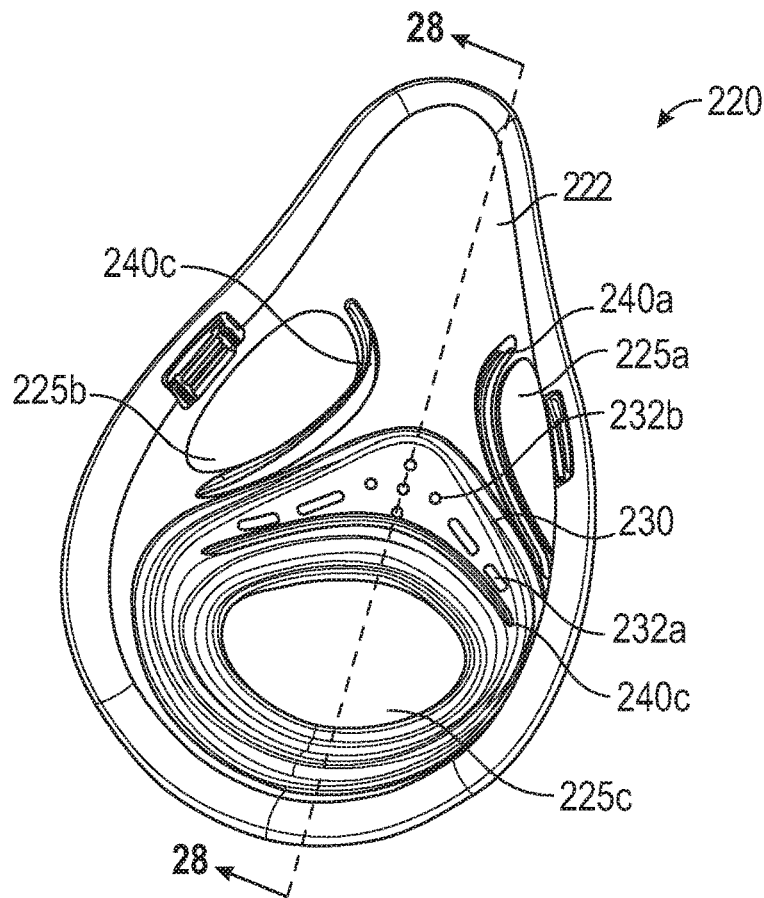
FIG. 27 illustrates a rear perspective view of a respiration sensor mask device, according to some embodiments.
Figure 28:
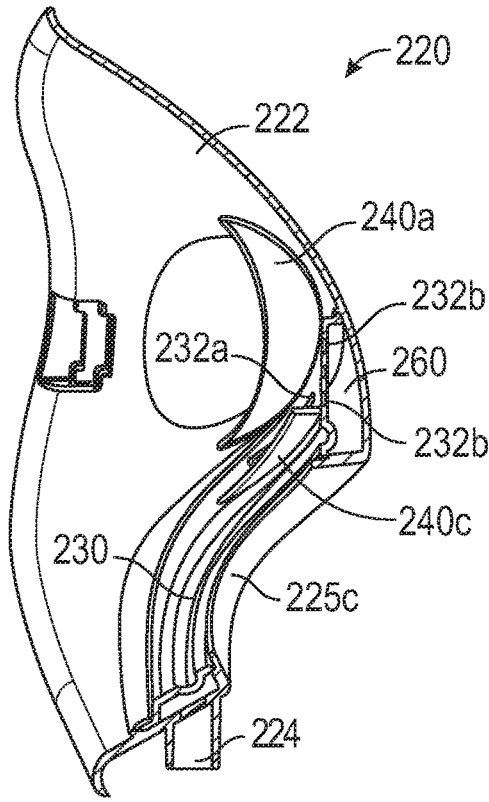
FIG. 28 illustrates a cross-sectional view of the respiration sensor mask device of FIG. 27 taken along section line 24-24.

Referring to FIGS. 27 and 28, an embodiment of a respiration mask assembly 220 is illustrated that can provide a fluid into the interior volume of the mask 222 and/or receive a sample of a fluid from the interior volume of the mask 222, without impeding operation of the respiration sensor device 210. The respiration mask assembly 220 includes fluid ports 232a, 232b and fluid fences 240a, 240b, 240c that can provide a fluid into the interior volume of the mask 222 adjacent to the patient's nares and mouth when the respiration sensor mask device 200 is affixed to the patient's face.

The respiration mask assembly 220 includes a mask 222, a fluid manifold 230, and fluid fences 240a, 240b, 240c. The fluid ports 232a, 232b can be formed in a fluid manifold 230 disposed within the interior volume of the mask 222. A fluid channel 260 is formed between an inner surface of the mask 222 and the fluid manifold 230. The fluid channel 260 directs a fluid from the supply fluid port 224 to the fluid ports 232a, 232b formed through the gas manifold 230. The fluid ports 232a, 232b and fluid fences 240a, 240b, 240c are configured to direct a fluid flow toward a patient and to resist interference with operation of the respiration sensor device 210 caused by fluid moving into or out of the interior volume of the mask.

Figure 29:
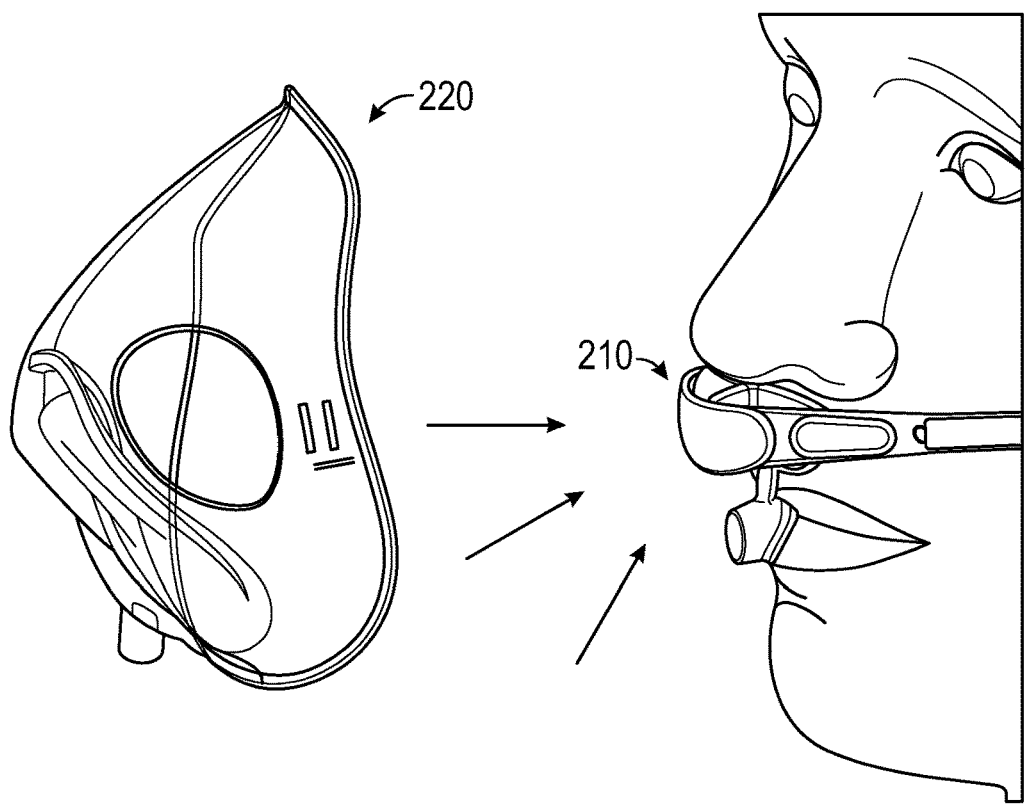
FIG. 29 illustrates a exploded side perspective view of a fluid flow between a respiration mask assembly and a respiration sensor device, according to some embodiments.

Referring also to FIG. 29, the fluid ports 232a, 232b create and direct fluid flows and/or flow paths, in the direction of the arrows, towards the nose and/or mouth of the patient and away from the vent openings 225a, 225b, 225c. The fluid ports 232a, 232b can be vectored to direct a gas flow in a desired direction. During operation, the fluid ports 232a, 232b can utilize fluid dynamic characteristics to generate "curtain effect" gas flow (e.g., a distributed flow) or a gas curtain that directs gas flow towards the patient's mouth and nose while acting as a barrier or boundary to environmental gases entering the interior volume of the mask 222 via the vent openings 225a, 225b, 225c. In some embodiments, the boundary formed by the gas curtain can be disposed between or adjacent to the vent openings 225a, 225b, 225c and the patient's breathing anatomy, such as the patient's mouth and nose.

As shown, the fluid ports 232a, 232b can include various geometric features to direct the gas flow as desired. For example, the fluid ports 232a can have an elongated slot geometry, cross-section, or profile. Optionally, the fluid ports 232a can further include rounded edges. In some embodiments, the fluid ports 232a can be tapered to direct gas flow therethrough. For example, the fluid ports 232a can be tapered axially tapered towards the patient. Further, the fluid ports 232b can have a circular geometry, cross-section, or profile. In some embodiments, the fluid ports 232b can be tapered to direct gas flow therethrough. For example, the fluid ports 232b can be tapered axially tapered towards the patient.

The fluid ports 232a, 232b can be arranged to promote the curtain effect gas flow and areas of high gas concentration. For example, the fluid ports 232a can be disposed on the fluid manifold 230 generally circumferentially around an upper edge of the vent opening 225c. Further, the fluid ports 232b can be clustered together on the fluid manifold 230 at an upper edge of the vent opening 225c. In some embodiments of the present disclosure, any of the fluid ports 232a, 232b can positioned between the vent openings 225a, 225b, 225c. In some embodiments, the fluid ports 232b can be flanked by the fluid ports 232a. Optionally, the fluid ports 232a, 232b can be configured to follow the shape of a patient's upper lip region to the corners of the patient's mouth.

The fluid fences 240a, 240b, 240c can promote the curtain effect gas flow and areas of high gas concentration. The fluid fences 240a, 240b, 240c can also prevent entrainment of environmental air into the interior volume of the mask. The fluid fences 240a, 240b, 240c extend from the mask 222 and/or the fluid manifold 260 into the interior volume of the mask. The fluid fences 240a, 240b, 240c can be disposed generally between the fluid ports 232a, 232b and the vent openings 225a, 225b, 225c.

In some applications, the fluid fences 240a, 240b can be disposed on either side of the patient's nose and the fluid fence 240c can be disposed below the patient's nose to promote curtain effect gas flow and to maintain a gas concentration in the area adjacent to the patient's nose and mouth while preventing or limiting the entrainment of environmental gases from the vent openings 225a, 225b, 225c. Further, in some embodiments, the lower fluid fence 240c can promote curtain effect gas flow around the lower vent opening 225c and gas concentration in the area adjacent to the patient's mouth. During operation, the gas curtain and the boundary formed by the gas flow can create one or more protected volume of gas in the interior volume of the mask. The protected volume of gas can resist or reduce mixing with ambient or environmental gases.

When the respiration sensor device 210 and the respiration sensor mask device 200 are coupled together during use with a patient, e.g., with the respiration sensor device 210 between the patient and the mask 222, each of the respiration sensor device 210 and respiration sensor mask device 200 can operate as desired. In use, mask 222 can operate as desired (e.g., provide oxygenation and/or gas sampling) without being affected by placement of the respiration sensor device 210 between the patient and the mask 222. In use, the respiration sensor device 210 can operate as desired (e.g., perform respiration measurement and receive data) without being affected by placement of or oxygenation by the mask 222.

In some embodiments, the respiration sensor device 210 can measure ambient temperature and temperature change data caused by fluid flow from the respiration sensor mask device 200. The respiration sensor device 210 can use the measured data to improve breathing signal amplitude measurement performance.

In some aspects of the present disclosure, any of the position of the respiration sensor device 210 in the interior volume of the respiration sensor mask device 200, the fluid ports 232a, 232b and fluid fences 240a, 240b, 240c of the respiration sensor mask device 200, and the housing 112, the base 114, and/or the shroud 116 of the respiration sensor device 210 permit desired operation of the respiration sensor device 210 and the respiration sensor mask device 200.

Any of the fluid ports 232a, 232b and the fluid fences 240a, 240b, 240c result in the creation of an area of high gas concentration in the interior volume of the mask without requiring the gas to be directed into the interior volume of the mask at a high velocity. For example, the velocity at which a gas is directed into the interior volume of the mask of the present application is less than a convention mask. The area of high gas concentration reduces or prevents unintended signal changes by the respiration sensor device 210, while permitting the patient to breath or draw from the gas during inhalation.

The respiration sensor device 210 and the respiration mask assembly 220 can resist fluid moving into or out of the mask from intersecting the oral thermistor 43 or nasal thermistors 41, 42 of the respiration sensor device 210. In some embodiments, features of the respiration sensor device 210, such as the cover 105, the housing 112, the base 114, and/or the shroud 116 can reduce or obstruct unintentional engagement of fluid moving into or out of the mask against the thermistors 41, 42, 43. The respiration sensor device 210 and respiration mask assembly 220 are configured so that the thermistors 41, 42, 43 are exposed to fluid moving due to inhalation or exhalation by the patient; however, the thermistors 41, 42, 43 are not exposed to fluid directed into the mask from the fluid ports 232a, 232b.

Aspects of the present disclosure are also demonstrated by the following testing results. Oxygenation performance of the respiration sensor mask device 200 was measured at the patient's nasal cavity and the mouth when supplying 100% O2 by volume at 10 liters/minute. When using the respiration sensor device 210 and the respiration sensor mask device 200 together, the measured percent oxygen volume at the patient's nasal cavity was reduced approximately 0%, relative to the measured percent oxygen volume at the patient's nasal cavity when the respiration sensor mask device 200 was used alone. When using the respiration sensor device 210 and the respiration sensor mask device 200 together, the measured percent oxygen volume at the patient's mouth was reduced approximately 2%, relative to the measured percent oxygen volume at the patient's mouth when the respiration sensor mask device 200 was used alone.

Testing of the respiration sensor device 210 was conducted using a simulated patient apparatus. The simulated patient apparatus included a head, which replicates a patients nasal and oral cavities, and pump, which directs a gas flow through nasal and oral cavities of the head. The testing was conducted using oxygenation by the respiration sensor mask device 200 at flow rates of 1 liter/minute, 5 liters/minute, 10 liters/minute, and 15 liters/minute. The respiration sensor device 210 performance was measured with and without the respiration sensor mask device 200. The following table provides approximate signal amplitude change when using the respiration sensor device 210 and the respiration sensor mask device 200 together, relative to change when the respiration sensor device 210 was used alone.

| Breathing through nose and mouth | | | |
|---|---|---|---|
| Flow [l/min] | Approximate change in signal amplitude for left nasal sensor | Approximate change in signal amplitude for right nasal sensor | Approximate change in signal amplitude for mouth sensor(s) |
| 1 | 5% | 21% | 4% |
| 5 | 2% | 9% | 9% |
| 10 | 1% | 10% | 5% |
| 15 | 2% | 4% | 1% |

Figure 30:
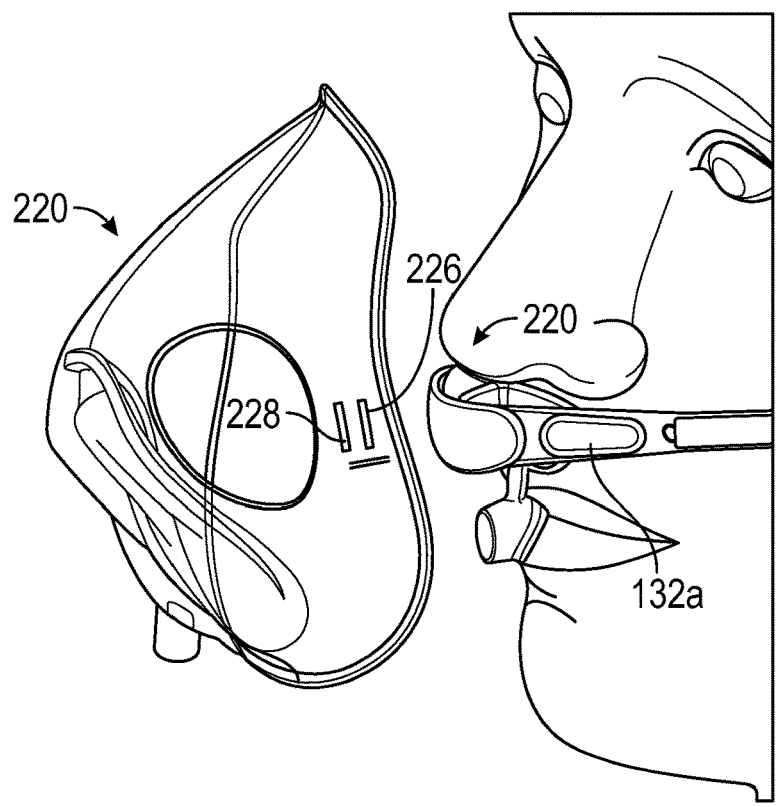
FIG. 30 illustrates a side perspective view of a respiration mask assembly being coupled with a respiration sensor device, according to some embodiments.

Referring to FIG. 30, the respiration mask assembly 220 can be coupled with the respiration sensor device 210 by engaging any of the connection member openings 226 and the support member openings 228 with the engagement pad 132a. In some aspects, the engagement pad 132a, or a portion thereof, can be received into the connection member openings 226 and/or the support member openings 228. In some embodiments, the housing is coupled to a first portion of the engagement pad 132a and the respiration mask assembly 220 is coupled to a second portion of the engagement pad 132a. In some aspects of the present disclosure, the first portion of the engagement pad 132a is a proximal or anterior portion and the second portion of the engagement pad 132a is a distal or posterior portion.

Figure 31A:
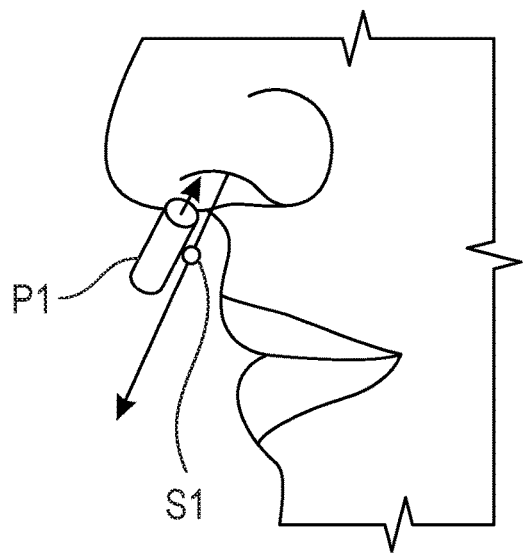
FIG. 31A illustrates a side plan view of a gas flow moving toward and away from a patient's nasal cavity.
Figure 31B:
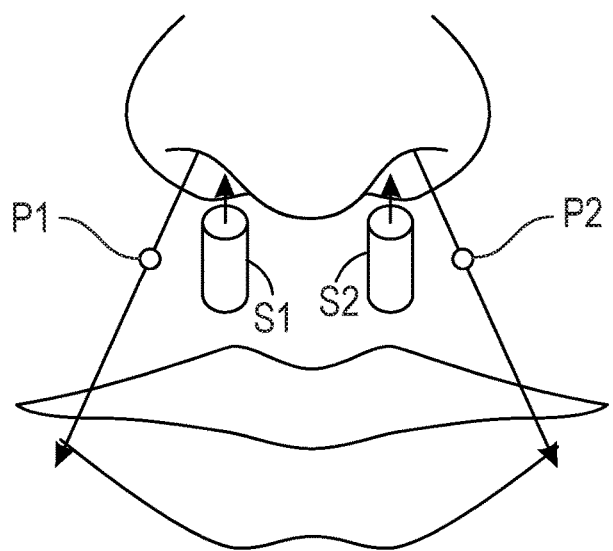
FIG. 31B illustrates a front plan view of a gas flow moving toward and away from a patient's nasal cavity.

Referring to FIG. 31A to 32B, the position of features of the present disclosure are illustrated relative to a patient's nares. FIG. 31A illustrates a nasal inhalation flow passage P1 positioned anterior to a portion of the subjects face. The nasal inhalation flow passage P1 is positioned proximal to the patient's philtrum, between the nose and upper lip. A sensor S1 of a respiration sensor device is positioned posterior to the nasal inhalation flow passage P1. The sensor is positioned between the nasal inhalation flow passage P1 and the patient's face. FIG. 31B illustrates a nasal inhalation flow passage P1, P2 of a nasal cannula positioned proximal to a septum of the subject's nares. A sensor S1, S2 of a respiration sensor device is positioned laterally outward relative to the nasal inhalation flow passage P1, P2. In some embodiments, first and second nasal inhalation flow passages P1, P2 are positioned between first and second sensors S1, S2.

The sensor and an outlet of the nasal inhalation flow passage are positioned so that a fluid flow from the nasal inhalation flow passage does not intersect of interfere with operation of the sensor. In contrast, if the sensor is exposed to unintended fluid flow from the nasal inhalation flow passage, the ability to distinguish patient breathing from flow of nasal inhalation flow passage may be reduced. In some embodiments, the outlet of the nasal inhalation flow passage is positioned between the sensor and the patient's nares.

The fluid from the nasal inhalation flow passages moves in direction toward the patient's nares. The direction of fluid from each of the first and second nasal inhalation flow passages can be parallel relative to each other, or can be transverse relative to each other. When the direction of fluid from each of the first and second nasal inhalation flow passages is transverse, the fluid flow is directed toward the patient's septum.

Figure 32A:
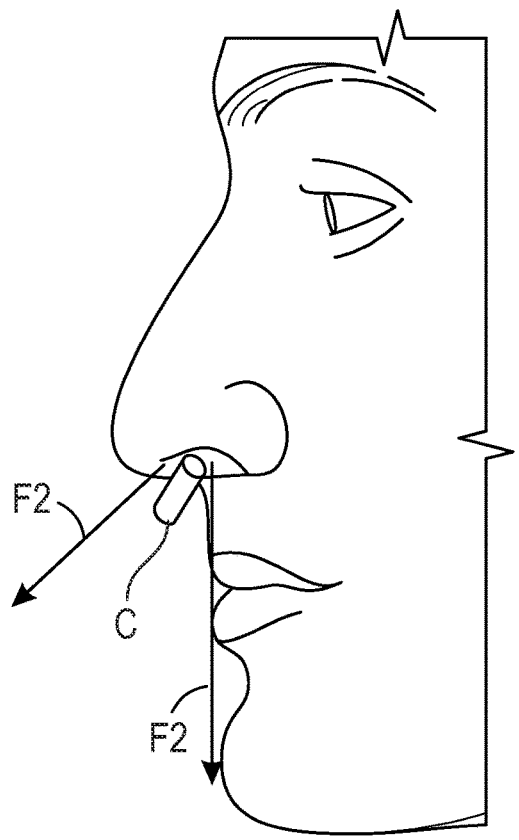
FIG. 32A illustrates a side plan view of a gas flow moving away from a patient's nasal cavity.
Figure 32B:
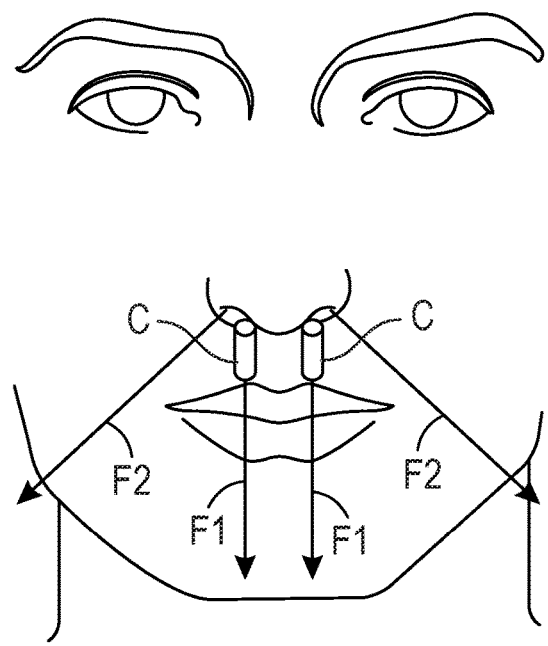
FIG. 32B illustrates a front plan view of a gas flow moving away from a patient's nasal cavity.

FIGS. 32A and 32B illustrate the inlet of cannula C relative to a patient's nares, as well as a fluid flow F2 directed away from the patient's nares. The fluid flow moving away from the patient's nares moves along an axial direction F1 of the cannula and in a direction that is transverse F2 relative to the axial direction of the cannula.

Methods of using a respiration sensor cannula device and/or a respiration sensor mask device are provided, in some embodiments. For example, a respiration sensor device may be initially positioned on the face of a subject or patient. A fluid delivery device (e.g., nasal cannula device, respiratory mask device) may then be connected to the respiration sensor device. In another step, the currently connected fluid delivery device may be removed and replaced with a different fluid delivery device. For example, a nasal cannula device may be uncoupled and removed from the respiration sensor device while the respiration sensor device is in place on a patient's face, and then a respiratory mask device may be connected to the same respiration sensor device in place on the patient's face. In another example, a respiratory mask device may be uncoupled and removed from the respiration sensor device in place on a patient's face, and then a nasal cannula device may be connected to the same respiration sensor device in place on the patient's face.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A respiration sensor cannula device comprising: a base and a housing comprising first and second nasal exhalation flow passages, the first and second nasal exhalation flow passages are aligned in parallel to one another with respect to a nasal respiratory flow direction; the housing comprising first and second openings in an outer surface of the housing, and first and second nasal inhalation flow passages extending from the first and second openings, respectively, wherein the first and second openings are configured to receive a gas from a fluid delivery tube.

Clause 2. The respiration sensor cannula device of Clause 1, wherein end portions of first and second fluid delivery tubes are fluidly coupled to the first and second openings, respectively, to provide a fluid to a subject's nares.

Clause 3. The respiration sensor cannula device of any of Clauses 1 and 2, further comprising a cover disposed on the outer surface of the housing.

Clause 4. The respiration sensor cannula device of Clause 3, wherein the cover comprises at least one opening configured to receive a portion of the fluid delivery tube.

Clause 5. The respiration sensor cannula device of Clause 4, wherein the cover is sized and shaped to direct a fluid flow from the fluid delivery tube into at least one of the first and second nasal inhalation flow passages.

Clause 6. The respiration sensor cannula device of any of Clauses 1 to 5, wherein the first and second openings in the outer surface of the housing are configured to receive first and second nasal inhalation flow passages through the first and second openings, respectively.

Clause 7. The respiration sensor cannula device of any of Clauses 1 to 7, further comprising a placement band coupled to any of the base and the housing, wherein the placement band is configured to position the respiration sensor cannula device on a subject's head.

Clause 8. The respiration sensor cannula device of Clause 7, further comprising an engagement pad having a standoff extending between the base and the engagement pad, wherein the housing is coupled to base by slideably engaging a slot in the housing with the standoff.

Clause 9. The respiration sensor cannula device of Clause 8, wherein the engagement pad is configured to support the fluid delivery tube.

Clause 10. The respiration sensor cannula device of Clause 9, further comprising a cover disposed on the outer surface of the housing, wherein the cover comprises an opening configured to receive the fluid delivery tube, wherein the tube is fixedly disposed between the cover and the engagement pad.

Clause 11. The respiration sensor cannula device of any of Clauses 1 to 10, further comprising first and second nasal thermistors, wherein the first and second nasal thermistors extend into each of the first and second nasal exhalation flow passages, respectively.

Clause 12. The respiration sensor cannula device of Clause 11, further comprising a shroud disposed between the housing and the base, wherein the shroud comprises an extension that separates an interior volume between the housing and the base into the first and second nasal exhalation flow passages.

Clause 13. The respiration sensor cannula device of any of Clauses 1 to 12, further comprising an oral flow passage and an oral thermistor, the oral flow passage disposed transverse to the first and second nasal exhalation flow passages, along an oral respiratory flow direction.

Clause 14. The respiration sensor cannula device of any of Clauses 1 to 13, wherein the first and second nasal inhalation flow passages are formed, at least in part, by a wall that extends from the housing toward the base to define an open top of each of the first and second nasal inhalation flow passages.

Clause 15. The respiration sensor cannula device of Clause 14, wherein a cross-sectional area defined by the open top of each of the first and second nasal inhalation flow passages is greater than a cross-sectional area defined by the openings.

Clause 16. A respiration sensor cannula device comprising: a base and a housing comprising first and second nasal exhalation flow passages, the first and second nasal exhalation flow passages are aligned in parallel to one another with respect to a nasal respiratory flow direction; first and second openings in an outer surface of the housing; and first and second nasal inhalation flow passages; wherein the housing is configured to fluidly couple with a nasal cannula assembly, and wherein the first and second openings are configured to receive the first and second nasal inhalation flow passages therethrough, respectively.

Clause 17. A respiration sensor mask device comprising: a base and a housing comprising first and second nasal exhalation flow passages, the housing comprising a connection recess, wherein the first and second nasal exhalation flow passages are aligned in parallel to one another with respect to a nasal respiratory flow direction; a connection band comprising a connection member extending from the connection band, wherein the connection member is configured to couple with the connection recess; a respiration mask coupled between the connection band and the housing.

Clause 18. The respiration sensor mask device of Clause 17, wherein the connection band is configured to be disposed outside of an exterior surface of the respiration mask and the connection member is configured to extend through an opening in the respiration mask.

Clause 19. The respiration sensor mask device of Clause 18, wherein the connection band further comprises a support member extending from the connection band, the support member configured to engage against a portion of the housing.

Clause 20. The respiration sensor mask device of Clause 19, wherein the connection band is configured to be disposed outside of an exterior surface of the respiration mask and the support member is configured to extend through an opening in the respiration mask.

Clause 21. The respiration sensor mask device of any of Clauses 17 to 20, further comprising first and second nasal thermistors, wherein the first and second nasal thermistors extend into each of the first and second nasal exhalation flow passages, respectively.

Clause 22. The respiration sensor mask device of any of Clauses 17 to 21, further comprising an oral flow passage and an oral thermistor, the oral flow passage disposed transverse to the first and second nasal exhalation flow passages, along an oral respiratory flow direction.

Clause 23. The respiration sensor mask device of any of Clauses 17 to 22, further comprising a placement band coupled to any of the base and the housing, wherein the placement band is configured to position the respiration sensor mask device on a subject's face.

Clause 24. The respiration sensor mask device of any of Clauses 17 to 23, wherein the connection band is configured to be disposed outside of an exterior surface of the respiration mask and the connection band is shaped to curve around at least a portion of an opening in the respiration mask.

Clause 25. A method of using a respiration sensor device with a fluid delivery device, the method comprising: placing the respiration sensor device on a subject, the respiration sensor device having a base and a housing comprising first and second nasal exhalation flow passages that are disposed in parallel to one another with respect to a nasal respiratory flow direction; positioning the respiration sensor device so that first and second nasal thermistors in the respective first and second nasal exhalation flow passages receive exhalations from the subject's nares; connecting the fluid delivery device to the respiration sensor device, wherein the respiration sensor device and the fluid delivery device are disposed as a unit on the subject's face, and wherein the fluid delivery device comprises any of a cannula or a respiration mask; replacing the fluid delivery device with the other of the cannula or the respiration mask without removing the respiration sensor device from the subject.

Clause 26. The method of Clause 25, wherein the respiration mask comprises coupling a connection band to the housing of the respiration sensor device with the mask positioned between the respiration sensor and the connection band.

Clause 27. The method of Clause 26, further comprising: disconnecting the respiration mask from the respiration sensor device by disengaging the connection member from the housing; removing the respiration mask from the subject's face; and connecting a nasal cannula assembly to the respiration sensor device by one of: inserting first and second nasal inhalation flow passages of the nasal cannula assembly into first and second openings in an outer surface of a housing of the respiration sensor device, and inserting a tube from the nasal cannula assembly into a tube opening of a cover disposed on an outer surface of the housing of the respiration sensor device, wherein the cover directs a fluid flow from the tube into a nasal inhalation flow passage in the housing.

Clause 28. The method of any of Clauses 25 to 27, wherein connecting the fluid delivery device to the respiration sensor device comprises coupling the respiration mask to a first portion of an engagement pad of the base, and wherein the housing is coupled to a second portion of the engagement pad.

Clause 29. The method of any of Clauses 25 to 28, wherein replacing the fluid delivery device comprises separating a delivery tubing from the cannula and coupling the respiration mask to the respiration sensor device without removing a cover and the housing of the respiration sensor device.

Clause 30. A method of using a respiration sensor device with a fluid delivery device, the method comprising: providing a respiration sensor device comprising first and second nasal exhalation flow passages, the first and second nasal exhalation flow passages are aligned in parallel to one another with respect to a nasal respiratory flow direction; coupling a fluid delivery device comprising a respiration mask to the respiration sensor device such that the respiration sensor device is positioned within an interior volume of the respiration mask, the respiration mask configured to provide an area of higher gas concentration in a first portion of the interior volume of the respiration mask, relative to a second portion of the interior volume of the respiration mask, wherein at least a portion of the respiration sensor device is positioned in the first portion of the interior volume of the respiration mask.

Clause 31. The method of clause 30, wherein the respiration sensor device comprises a cover and a sensor, the cover positioned between a sensor and the respiration mask to resist a fluid flow from the respiration mask toward the sensor.

Clause 32. The method of clause 30, wherein the respiration mask comprises a fence configured to provide a curtain effect for fluid moving toward the first portion of the interior volume of the respiration mask, the fence extending in a first direction into the interior volume of the respiration mask to resist movement of a fluid flow away from the first portion of the interior volume of the respiration mask.

Clause 33. The method of any of Clauses 30 and 32, wherein a flow rate of fluid moving in the first portion of the interior volume of the respiration mask is greater than a flow rate of fluid moving in the second portion of the interior volume of the respiration mask.

Clause 34. A method of using a respiration sensor device with a fluid delivery device, the method comprising: providing a nasal inhalation flow passage of a nasal cannula anterior to a portion of the subject's face, between the nose and upper lip of the subject; providing a sensor of a respiration sensor device posterior to the nasal inhalation flow passage; wherein a fluid flow path from the nasal inhalation flow passage toward a subject's nare does intersect the sensor.

Clause 35. The method of clause 34, wherein an outlet of the nasal inhalation flow passage is between the sensor and the subject's nares.

Clause 36. A method of using a respiration sensor device with a fluid delivery device, the method comprising: providing a nasal inhalation flow passage of a nasal cannula proximal to a septum of the subject's nares; providing a sensor of a respiration sensor device laterally outward relative to the nasal inhalation flow passage; wherein a fluid flow path from the nasal inhalation flow passage toward a subject's nare does intersect the sensor.

Clause 37. The method of clause 36, wherein an outlet of the nasal inhalation flow passage is between the sensor and the subject's nares.

Clause 38. A respiration sensor system comprising: a respiration sensor device comprising an attachment mechanism configured to couple with any of a nasal cannula assembly or and respiration mask, the respiration sensor device comprising first and second nasal exhalation flow passages; wherein the respiration sensor device is configured to remain worn by a patient during interchange of the nasal cannula assembly and the respiration mask.

Clause 39. The system of Clause 38, wherein the respiration sensor device is configured to remain engaged against a patient, with the first and second nasal exhalation flow passages aligned with a nasal respiratory flow direction of the patient, when interchanging between any of the nasal cannula assembly and the respiration mask.

Clause 40. The system of any of Clauses 38 and 39, further comprising a nasal cannula assembly, wherein the nasal cannula assembly comprises nasal inhalation flow passages configured to direct a fluid toward a patient's nose.

Clause 41. The system of any of Clauses 38 to 40, further comprising a respiration mask, wherein the respiration mask comprises a fluid port configured to direct a fluid into an interior volume of the mask.

Further Consideration

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiments described herein as "exemplary" is not necessarily to be construed as preferred or advantageous over other embodiments.

In one or more aspects, the terms "about," "substantially," and "approximately" may provide an industry-accepted tolerance for their corresponding terms and/or relativity between items.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A respiration sensor cannula device comprising:
a base and a housing, coupled to the base to form first and second nasal flow passages between the housing and the base, the first and second nasal flow passages are aligned in parallel to one another with respect to a nasal respiratory flow direction and form a nasal inlet at a top portion and a nasal outlet at a bottom portion of the cannula device;
the housing comprising first and second openings in an outer surface of the housing, and first and second nasal inhalation flow passages extending from the first and second openings, respectively, wherein the first and second openings are configured to receive a gas from a fluid delivery tube, and direct the gas toward the nasal inlet; and
a first nasal thermistor in the first nasal flow passage, and a second nasal thermistor in the second nasal flow passage.

2. The respiration sensor cannula device of claim 1, wherein end portions of first and second fluid delivery tubes are fluidly coupled to the first and second openings, respectively, to provide a fluid to a subject's nares.

3. The respiration sensor cannula device of claim 1, further comprising a cover disposed on the outer surface of the housing, wherein the cover comprises at least one opening configured to receive a portion of the fluid delivery tube.

4. The respiration sensor cannula device of claim 1, wherein the first and second openings in the outer surface of the housing are configured to receive first and second nasal inhalation flow passages through the first and second openings, respectively.

5. The respiration sensor cannula device of claim 1, further comprising a placement band coupled to any of the base and the housing, wherein the placement band is configured to position the respiration sensor cannula device on a subject's head.

6. The respiration sensor cannula device of claim 5, further comprising an engagement pad having a standoff extending between the base and the engagement pad, wherein the housing is coupled to base by slideably engaging a slot in the housing with the standoff.

7. The respiration sensor cannula device of claim 1, wherein the first and second nasal thermistors extend into each of the first and second nasal exhalation-flow passages, respectively.

8. The respiration sensor cannula device of claim 1, further comprising a shroud disposed between the housing and the base, wherein the shroud comprises an extension that separates an interior volume between the housing and the base into the first and second nasal flow passages.

9. The respiration sensor cannula device of claim 1, further comprising an oral flow passage and an oral thermistor, the oral flow passage disposed below the first and second nasal flow passages, the oral respiratory flow direction being transverse to the nasal respiratory flow direction.

10. The respiration sensor cannula device of claim 1, wherein the first and second nasal inhalation flow passages are formed, at least in part, by a wall that extends from the housing toward the base to define an open top of each of the first and second nasal inhalation flow passages.

11. The respiration sensor cannula device of claim 10, wherein a cross-sectional area defined by the open top of each of the first and second nasal inhalation flow passages is greater than a cross-sectional area defined by the openings.

12. A respiration sensor mask device comprising:
a base and a housing, coupled to the base to form first and second nasal flow passages between the housing and the base, the housing comprising a connection recess, wherein the first and second nasal flow passages are aligned in parallel to one another with respect to a nasal respiratory flow direction and form a nasal inlet at a top portion and a nasal outlet at a bottom portion of the cannula device, and first and second nasal thermistors are positioned in the first and second nasal flow passages, respectively;
a connection band and a connection member extending from the connection band, wherein the connection member is configured to couple with the connection recess; and
a respiration mask coupled between the connection band and the housing.

13. The respiration sensor mask device of claim 12, wherein the first and second nasal thermistors extend into each of the first and second nasal flow passages, respectively.

14. The respiration sensor mask device of claim 12, further comprising an oral flow passage and an oral thermistor, the oral flow passage disposed below the first and second nasal flow passages, the oral respiratory flow direction being transverse to the nasal respiratory flow direction.

15. The respiration sensor mask device of claim 12, wherein the connection band is configured to be disposed outside of an exterior surface of the respiration mask and the connection band is shaped to curve around at least a portion of an opening in the respiration mask.

16. A method of using a respiration sensor device with a fluid delivery device, the method comprising:
placing the respiration sensor device on a subject, the respiration sensor device having a base and a housing, the housing coupled to the base to form first and second nasal flow passages, between the housing and the base, that are disposed in parallel to one another with respect to a nasal respiratory flow direction and form a nasal inlet at a top portion and a nasal outlet at a bottom portion of the cannula device;
positioning the respiration sensor device so that first and second nasal thermistors in the respective first and second nasal flow passages receive exhalations from the subject's nares;
connecting the fluid delivery device to the respiration sensor device, wherein the respiration sensor device and the fluid delivery device are disposed as a unit on the subject's face, and wherein the fluid delivery device comprises any of a nasal cannula assembly or a respiration mask; and
replacing the fluid delivery device with the other of the nasal cannula assembly or the respiration mask without removing the respiration sensor device from the subject.

17. The method of claim 16, wherein the respiration mask comprises coupling a connection band to the housing of the respiration sensor device with the respiration mask positioned between the respiration sensor device and the connection band.

18. The method of claim 17, further comprising:
disconnecting the respiration mask from the respiration sensor device by disengaging the connection band from the housing;
removing the respiration mask from the subject's face; and
connecting a nasal cannula assembly to the respiration sensor device by one of:
inserting first and second nasal inhalation flow passages of the nasal cannula assembly into first and second openings in an outer surface of a housing of the respiration sensor device, and
inserting a tube from the nasal cannula assembly into a tube opening of a cover disposed on an outer surface of the housing of the respiration sensor device, wherein the cover directs a fluid flow from the tube into a nasal inhalation flow passage in the housing.

19. The method of claim 16, wherein connecting the fluid delivery device to the respiration sensor device comprises coupling the respiration mask to a first portion of an engagement pad of the base, and wherein the housing is coupled to a second portion of the engagement pad.

20. The method of claim 16, wherein replacing the fluid delivery device comprises separating a delivery tubing from the nasal cannula assembly and coupling the respiration mask to the respiration sensor device without removing a cover and the housing of the respiration sensor device.

* * * * *